US008057989B2

(12) United States Patent  (10) Patent No.: US 8,057,989 B2
Yam et al.  (45) Date of Patent: Nov. 15, 2011

(54) LABEL-FREE OPTICAL SENSING AND CHARACTERIZATION OF BIOMOLECULES BY $D^8$ OR $D^{10}$ METAL COMPLEXES

(75) Inventors: Vivian Wing-Wah Yam, Hong Kong (HK); Cong Yu, Hong Kong (HK); Kenneth Hoi-Yiu Chan, Kowloon (HK); Keith Man-Chung Wong, Kowloon (HK)

(73) Assignee: The University of Hong Kong, Hong Kong (HK)

( * ) Notice: Subject to any disclaimer, the term of this patent is extended or adjusted under 35 U.S.C. 154(b) by 1336 days.

(21) Appl. No.: 11/625,109

(22) Filed: Jan. 19, 2007

(65) Prior Publication Data

US 2007/0190549 A1  Aug. 16, 2007

Related U.S. Application Data

(60) Provisional application No. 60/772,090, filed on Feb. 10, 2006.

(51) Int. Cl.
*C12Q 1/68* (2006.01)
*C12Q 1/00* (2006.01)

(52) U.S. Cl. .............................................. 435/4; 435/6
(58) Field of Classification Search ....................... 435/6
See application file for complete search history.

(56) References Cited

U.S. PATENT DOCUMENTS

| 5,985,567 | A | 11/1999 | Rampal |
| 6,132,972 | A | 10/2000 | Shigemori et al. |
| 2001/0046670 | A1 | 11/2001 | Brookes |
| 2004/0033518 | A1 | 2/2004 | Wittwer et al. |
| 2004/0219556 | A1 | 11/2004 | Bazan et al. |
| 2005/0048485 | A1 | 3/2005 | Kurane et al. |
| 2005/0059042 | A1 | 3/2005 | Rothberg et al. |

FOREIGN PATENT DOCUMENTS

| CA | 2489922 | 6/2003 |
| GB | 2318791 | 5/1998 |
| JP | 61219400 | 9/1986 |
| JP | 11151100 | 6/1999 |
| JP | 2005000088 | 1/2005 |
| WO | 9846790 | 10/1998 |
| WO | 9942616 | 8/1999 |
| WO | 03091408 | 11/2003 |
| WO | 2004111602 | 12/2004 |

OTHER PUBLICATIONS

Ratilla (PhD Thesis Iowa State University, Ames Laboratory, U.S. DOE, Oct. 9, 1990).*
Remington's: the Science and Practice of Pharmacy, Nineteenth Edition, vol. 1, p. 806.*
Adamovich et al, *High Efficiency Single Dopant White Electrophosphorescent light emitting diodes*; New Journal of Chemistry, (2002), 26, 1171-1178.

Backburn et al.; *Nucleic Acids in Chemistry and Biology*; Oxford University Press, Oxford, (1996).
Bloomfield et al.; *Nucleic Acids: Structures, Properties, and Functions*; University Science Books, California, (2000).
Creighton; *Proteins: Structure and Molecular Properties*; W.H. Freeman and Company, New York, (1993).
Fasman ed.; *Circular Dichroism and the Conformational Analysis of Biomolecules*; Plenum Press, New York, (1996).
Gaylord et al.; *DNA Detection Using Water-Soluble Conjugated Polymers and Peptide Nucleic Acid Probes*; Proceedings of the National Academy of Sciences of the United States of America, (2002), 99, 10954-10957.
Goshe et al; *Supramolecular Recognition. Terpyridyl Palladium and Platinum Molecular Clefts and Their Association with Planar Platinum Complexes*; Journal of the American Chemical Society, (2003), 125,444-451.
Li et al.; *Label-Free Colorimetric Detection of Specific Sequences in Genomic DNA Amplified by the Polymerase Chain Reaction*; Journal of the American Chemical Society, (2004), 126, 10958-10961.
Yam et al.; *Luminescent Platinum (II) Terpyridyl Complexes: Effect of Counter Ions on Solvent-Induced Aggregation and Color Changes*; Chemistry—A European Journal, (2005), 11, 4535-4543.
Yam et al.; *Solvent-Induced Aggregation through Meta•••Metal/π•••π Interactions: Large Solvatochromism of Luminescent Organoplatinum (II) Terpryridyl Complexes*; Journal of the American Chemical Society, (2002), 124, 6506-6507.
Yam et al.; *Synthesis, Luminescence, Electrochemistry, and Ion-Binding Studies of Platinum (II) Terpyridyl Acetylide Complexes*; Organometallics, (2001) 20, 4476-4482.
Yu et al.; *Polymer-Induced Self-Assembly of Alkynlyplatinum(II) Terpyridyl Complexes by Metal•••Metal/π•••π Interactions*; Angewandte Chemie International Edition, (2005), 44, 791-794.
Vivian Wing-Wah Yam et al., Luminescent Platinum (Ii) Terpyridyl Complexes: Efect of Counter Ions on Solvent-Induced Aggregation and Color Changes; Chem Eur. J. (2005) 11, 4535-4543.
Nucleic Acids in Chemistry and Biology, Second Edition Edited by G. Michael Blackburn and Michael J. Gait; Oxford University Press 1996; Cover, Title Page and Table of Contents is attached.
Victor A. et al., Nucleic Acids, Structures, Properties, and Functions; University Science Books (2000); Cover, Title Page, and Table of Contents is attached.
Circular Dichroism and the Conformational Analysis of Biomolecules Edited by Gerald D. Fasman; (1996) Plenum Press, New York; Table of Contents is attached.
Thomas E. Creighton; Proteins: Structures and Molecular Properties, Second Edition; W.H. Freeman and Company, New York (1993); Table of Contents is attached.

* cited by examiner

*Primary Examiner* — Michael G Hartley
*Assistant Examiner* — Melissa Perreira
(74) *Attorney, Agent, or Firm* — Robert D. Katz; Cooper & Dunham LLP

(57) ABSTRACT

The present invention provides a composition for detecting and/or characterizing a multiple-charged biomolecule comprising a charged $d^8$ or $d^{10}$ metal complex, wherein the metal complex electrostatically binds to the multiple-charged biomolecule to induce aggregation and self-assembly of the metal complex through metal . . . metal interactions, π . . . π interactions, or a combination of both interactions. The present invention further provides assay methods and kits for label-free optical detection and/or characterization of biomolecules carrying multiple charges, e.g., single-stranded nucleic acids, polyaspartate, polyglutamate, using a composition comprising a charged $d^8$ or $d^{10}$ metal complex.

10 Claims, 26 Drawing Sheets

Complex 2

Complex 1

LABEL-FREE OPTICAL SENSING AND CHARACTERIZATION OF BIOMOLECULES BY $d^8$ OR $d^{10}$ METAL COMPLEXES

CROSS-REFERENCE TO RELATED APPLICATION

This application claims priority of U.S. Provisional Patent Application No. 60/772,090, filed Feb. 10, 2006, the entire contents of which are incorporated by reference herein.

FIELD OF THE INVENTION

The present invention relates to procedures and materials for label-free optical detection and characterization of biomolecules carrying multiple charges in a sample.

BACKGROUND OF THE INVENTION

Nucleic acids, either DNA or RNA, single-stranded or double-stranded, are the most fundamental and important class of biomolecules in a living cell. DNA encodes the genetic information that passes from generation to generation. Through transcription, the coded information is transferred to mRNA, which binds to ribosome (specific ribosomal RNA and protein complex). With the assistance of tRNA, which contains an anticodon and a specific amino acid, the carried information of mRNA is translated into a precise sequence of a polypeptide of 20 amino acids. Folding of the polypeptide into a well-defined three-dimensional structure gives the protein. Many classes of protein act as building blocks, enzymes, and regulation factors. Together with other classes of biomolecules, proteins are responsible for the buildup and proper function of a living cell.

Since nucleic acids carry multiple negatively charged phosphate functional groups, they are polyanions. Under physiological conditions, poly(aspartic acid) and poly(glutamic acid) form polycarboxylates, which are also polyanions. On the other hand, polylysine, polyarginine, and polyhistidine (in an acidic aqueous solution) carry multiple positive charges, and are considered polycations. Many proteins, when the solution pH is not at their isoelectric point (pI) value, carry net positive or negative multiple charges. In light of the above, methods that can detect and characterize biomolecules with multiple charges are of great importance, which can not only help us to understand how the cell functions, assist biological/biochemical research, but may also provide ways to facilitate biomedical research, clinical diagnosis, and new drug development.

The intriguing structural and bonding properties of square-planar $d^8$ or $d^{10}$ metal complexes have attracted long-standing interest, and more so recently with the growing interest in the spectroscopic properties associated with this class of metal complexes. These metal complexes are known to display a strong tendency towards the formation of highly-ordered extended linear chains or oligomeric structures in the solid state. The extent of the metal-metal interaction and the $\pi \ldots \pi$ stacking of the aromatic ligand have led to the observation of interesting spectroscopic and luminescence properties, and recent reports based on the utilization of these observations for molecular recognition, chemosensing, and optoelectronic applications have been made. (17, 23, 27)

A representative example of the class of the aforementioned $d^8$ or $d^{10}$ metal complexes is the alkynylplatinum(II) terpyridyl complexes (25, 26, 28). By changing the solvent polarity, or using a polyelectrolyte (a polyanion), namely polyacrylate, the $d^8$ or $d^{10}$ metal complexes are induced to aggregate and self-assemble, thereby creating observable dramatic changes in the UV/vis and emission spectra.

There are a number of assay methods available nowadays for the detection and characterization of multiple-charged biomolecules. However, most of the commonly used existing methods require sophisticated analytical techniques and expensive instrumentations. Many of these methods require labeling with a detectable group, which can be a radioisotope or a fluorescent substance, as well as hybridization procedures for nucleic acid detection. Hence, such methods usually demand high financial cost and are technically complicated and time-consuming.

The present invention provides a novel label-free assay method to sense and characterize multiple-charged biomolecules. Binding of the charged $d^8$ or $d^{10}$ metal complex to the biomolecule carrying opposite charges induces aggregation and self-assembly of the metal complex, and hence gives rise to remarkable UV/vis, emission, and CD intensity changes. The assay not only provides a means to detect the presence of multiple-charged biomolecules, but can also be used to study their secondary structure and structure/conformation changes.

SUMMARY OF THE INVENTION

In general, the present invention provides compositions, methods, and kits for detecting and/or characterizing biomolecules carrying multiple charges. A charged $d^8$ or $d^{10}$ metal complex is mixed with a biomolecule. Electrostatic binding of the charged metal complex to the oppositely charged biomolecule induces aggregation and self-assembly of the metal complex via metal-metal interactions and/or $\pi \ldots \pi$ stacking interactions of a corresponding coordinating ligand in the metal complex, which in turn creates remarkable optical property changes, such as UV/vis, emission, and CD intensity changes, to the metal complex (29).

The present invention provides a composition for detecting and/or characterizing a multiple-charged biomolecule comprising a charged $d^8$ or $d^{10}$ metal complex, wherein the metal complex electrostatically binds to the multiple-charged biomolecule to induce aggregation and self-assembly of the metal complex through metal . . . metal interactions, $\pi \ldots \pi$ interactions, or a combination of both interactions.

The present invention also provides an assay method for detecting the presence of a target multiple-charged biomolecule in a sample comprising: (a) combining a charged $d^8$ or $d^{10}$ metal complex, wherein the metal complex comprising at least one transition metal and at least one corresponding coordinating ligand, with the sample potentially containing the target multiple-charged biomolecule under conditions effective to allow the $d^8$ or $d^{10}$ metal complex and the target multiple-charged biomolecule to bind to each other by electrostatic interactions, and to allow subsequent self-assembly of a charged $d^8$ or $d^{10}$ metal complex aggregate; and (b) measuring optical properties of the charged $d^8$ or $d^{10}$ metal complex aggregate.

The present invention further provides a kit for use in detecting a multiple-charged biomolecule in a sample comprising (a) a composition comprising a charged $d^8$ or $d^{10}$ metal complex, wherein the metal complex electrostatically binds to the multiple-charged biomolecule to induce aggregation and self-assembly of the $d^8$ or $d^{10}$ metal complex through metal . . . metal interactions and $\pi \ldots \pi$ interactions; and (b) instructions for use.

DETAILED DESCRIPTION OF THE PREFERRED EMBODIMENTS

Definitions

Figure 1:
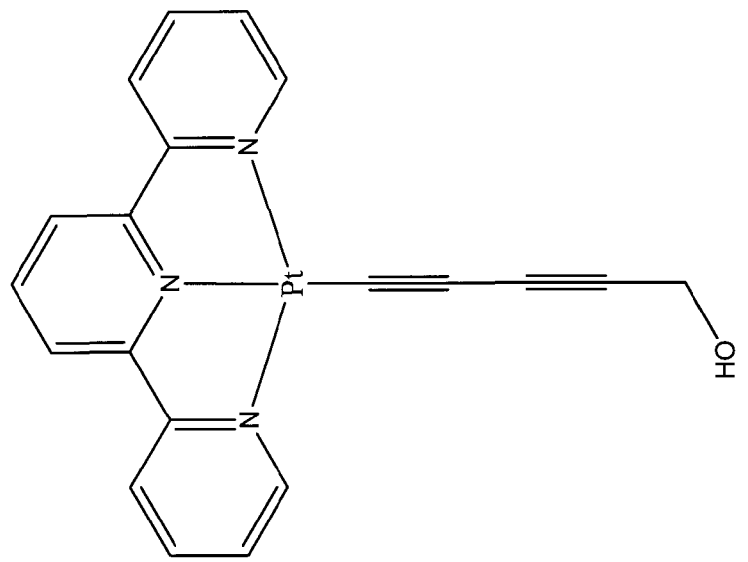
FIG. 1 shows two cationic $d^8$ metal complexes as illustrative examples.
Figure 1:
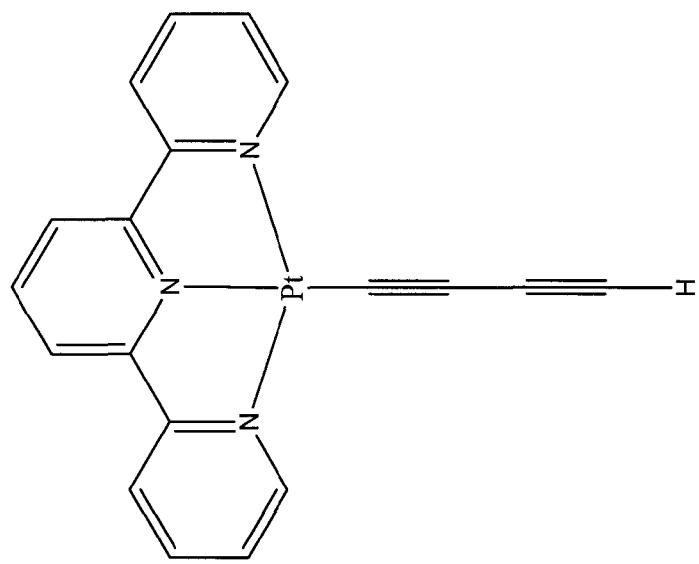

As used in this application, except as otherwise expressly provided, each of the following terms shall have the meaning set forth below:

The term "single-stranded nucleic acid" employed herein can be single-stranded DNA, RNA of any length, natural or artificial, any derivatives or their analogues as long as it carries negative charge and the nucleic base sequence. It can be part of a duplex DNA or RNA, part of any combination of DNA, RNA, protein, carbohydrate, lipid, a their derivatives. It may be freely distributed in solution, or immobilized onto the solid support surface. The nucleic acid can be directly obtained from a sample solution, or derived from amplified genes or gene fragments.

The term "protein" or "polypeptide" employed herein can be a protein of any length, natural or artificial, any derivatives or their analogues as long as it carries the basic peptide sequence. It can be part of any combination of DNA (double-stranded or single-stranded), RNA (double-stranded or single-stranded), protein, carbohydrate, lipid, and their derivatives. It may be freely distributed in solution, or immobilized onto a solid support surface.

The term "biomolecule" employed herein can be DNA, RNA, protein, carbohydrate, lipid, their combinations and derivatives carrying multiple charges. It may be freely distributed in solution, or immobilized onto a solid support surface.

The term "charged" employed herein can be either anionic or cationic.

The term "charged $d^8$ or $d^{10}$ metal complex aggregate" employed herein can be any metal complex that contains at least one metal center of $d^8$ or $d^{10}$ electronic configuration that carries a net positive or negative charge, which, in the vicinity of a biomolecule of opposite charge, can cause a local concentration enrichment of the metal complex, brought about by electrostatic interactions between the biomolecule and the metal complex.

The term "corresponding coordinating ligand" employed herein can be any donor ligand that forms a dative coordination bond to a metal center.

Embodiments Of The Invention

The present invention provides a composition for detecting and/or characterizing a multiple-charged biomolecule comprising a charged $d^8$ or $d^{10}$ metal complex, wherein the metal complex electrostatically binds to the multiple-charged biomolecule to induce aggregation and self-assembly of the metal complex through metal . . . metal interactions, $\pi \ldots \pi$ interactions, or a combination of both interactions.

In one embodiment, the charged $d^8$ or $d^{10}$ metal complex may comprise at least one transition metal and at least one corresponding coordinating ligand. A non-limiting list of examples of the transition metals contains platinum (Pt), gold (Au), palladium (Pd), rhodium (Rh), iridium (Ir), and silver (Ag), which are capable of participating in metal . . . metal interactions. A non-limiting list of examples of corresponding coordinating ligands contains aryl, alkyl, alkynyl, and their derivatives; nitrogen donor ligands including pyridine, bipyridine, terpyridine, polypyridine, arylpyridine, diarylpyridine, arylbipyridine, phenanthroline, diazine, triazine, phthalocyanine, imine, diimine, triimine, porphyrin, and their derivatives; sulphur, phosphorus, and oxygen donor ligands including phosphine, thiolate, carboxylate, and their derivatives. The corresponding coordinating ligand can also have the following structures:

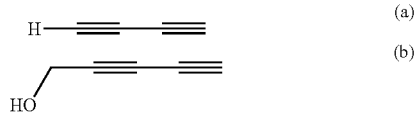

The charged $d^8$ or $d^{10}$ metal complex should carry at least one net positive or negative charge. Preferably, the metal complex has a planar structure or a partially planar structure, and at least one corresponding coordinating ligand is capable of $\pi \ldots \pi$ stacking interactions.

Preferably, the multiple-charged biomolecule should carry at least three net charges to induce the aggregation of the charged $d^8$ or $d^{10}$ metal complex.

The present invention also provides an assay method for detecting the presence or absence of a target multiple-charged biomolecule in a sample comprising: (a) combining a charged $d^8$ or $d^{10}$ metal complex, wherein the metal complex comprising at least one transition metal and at least one corresponding coordinating ligand, with the sample potentially containing the target multiple-charged biomolecule under conditions effective to allow the $d^8$ or $d^{10}$ metal complex and the target multiple-charged biomolecule to bind to each other by electrostatic interactions, and to allow subsequent self-assembly of a charged $d^8$ or $d^{10}$ metal complex aggregate; and (b) measuring optical properties of the charged $d^8$ or $d^{10}$ metal complex aggregate.

In one embodiment, the present invention provides a method for detecting the presence of a target single-stranded nucleic acid molecule in a sample solution. The target nucleic acid molecule can be analyzed directly, or can be amplified prior to the analysis. This method comprises combining a charged $d^8$ or $d^{10}$ metal complex with a sample solution potentially containing a target nucleic acid molecule, under conditions effective to allow at least one single-stranded nucleic acid to associate electrostatically with the $d^8$ or $d^{10}$ metal complex, and to allow subsequent self-assembly of the $d^8$ or $d^{10}$ metal complex; determining whether at least one single-stranded nucleic acid has electrostatically associated with the $d^8$ or $d^{10}$ metal complex, wherein self-assembly of the $d^8$ or $d^{10}$ metal complex, and subsequently the presence or absence of the target nucleic acid molecule, is indicated by changes in optical properties, such as colorimetric assay, photoluminescence assay, or CD spectrometry analysis.

In another embodiment, the present invention provides a method for characterizing the structural properties of a target single-stranded nucleic acid. This method comprises combining a single-stranded nucleic acid molecule, of which the structural properties have been well-characterized, and a charged $d^8$ or $d^{10}$ metal complex, under conditions effective to allow at least one single-stranded nucleic acid to associate electrostatically with the $d^8$ or $d^{10}$ metal complex to form an associating complex; and to allow subsequent self-assembly of the $d^8$ or $d^{10}$ metal complex, wherein self-assembly of $d^8$ or $d^{10}$ metal complex is recorded by its optical properties, such as colorimetric assay, photoluminescence assay, or CD spectrometry analysis. By conducting such experiments using different nucleic acid molecules of known structural properties, the combined set of information provides an effective way to deduce the structural properties of a target single-stranded nucleic acid.

In another embodiment, the present invention provides a method for detecting structural changes of a target single-stranded nucleic acid. This method can be carried out in two different ways. In one embodiment, the method comprises combining a target nucleic acid molecule and a charged $d^8$ or $d^{10}$ metal complex, under conditions effective to allow at least one single-stranded nucleic acid to associate electrostatically with the $d^8$ or $d^{10}$ metal complex to form an associating complex; and to allow subsequent self-assembly of the $d^8$ or $d^{10}$ metal complex, wherein self-assembly of $d^8$ or $d^{10}$ metal complex is recorded by its optical properties, such as colorimetric assay, photoluminescence assay, or CD spectrometry analysis. By conducting such experiments under different conditions, (e.g. different temperature, different ionic strength, or addition of compounds that may potentially cause structural property change of the target nucleic acid molecule), the optical properties are recorded, and changes in structural properties can then be deduced by comparing the changes in optical properties.

In a further embodiment, the method comprises exposing a target nucleic acid molecule to different conditions which may potentially induce structural property changes; combining the target nucleic acid molecule and a charged $d^8$ or $d^{10}$ metal complex, under conditions effective to allow at least one single-stranded nucleic acid to associate electrostatically with the $d^8$ or $d^{10}$ metal complex to form an associating complex; and to allow subsequent self-assembly of the $d^8$ or $d^{10}$ metal complex, wherein self-assembly of the $d^8$ or $d^{10}$ metal complex is recorded by its optical properties, such as colorimetric assay, photoluminescence assay, or CD spectrometry analysis. The recorded optical property changes can then be used to deduce the structural property changes of the target nucleic acid molecule.

In another embodiment, the present invention provides a method for detecting a mutation in a target nucleic acid molecule in a sample solution. This method comprises obtaining a sample solution containing the target nucleic acid molecule; combining a sample solution containing the target nucleic acid molecule, and a single-stranded nucleic acid probe that has a nucleotide sequence that hybridizes to a region of the target nucleic acid molecule that may contain one or several mutations, to form a test hybridization solution; combining a control solution including a new target nucleic acid molecule that does not contain mutation and the single-stranded nucleic acid probe that hybridizes perfectly to the target nucleic acid molecule, to form a control hybridization solution; exposing the test and control hybridization solutions, while maintaining the hybridization solutions at a temperature that is between the melting temperature of the first hybridization solution and the melting temperature of the second control hybridization solution, to a charged $d^8$ or $d^{10}$ metal complex under conditions effective to allow at least one unhybridized probe in the hybridization solutions to electrostatically associate with the $d^8$ or $d^{10}$ metal complex to form associating complex; and to allow subsequent self-assembly of the $d^8$ or $d^{10}$ metal complex, wherein self-assembly of $d^8$ or $d^{10}$ metal complex is recorded by its optical properties, such as colorimetric assay, photoluminescence assay, or CD spectrometry analysis; and determining whether the optical properties of the test and control hybridization solutions are substantially different, which forms the basis for indicating the presence or absence of mutation in the target nucleic acid molecule.

In another embodiment, the present invention provides a method for detecting the presence of a target multiple-charged protein in the sample solution. This method comprises combining a charged $d^8$ or $d^{10}$ metal complex with a sample solution potentially containing a target multiple-charged protein, under conditions effective to allow at least one target multiple-charged protein to associate electrostatically with the $d^8$ or $d^{10}$ metal complex, and to allow subsequent self-assembly of the $d^8$ or $d^{10}$ metal complex; and determining whether at least one target multiple-charged protein has electrostatically associated with the $d^8$ or $d^{10}$ metal complex, wherein self-assembly of the $d^8$ or $d^{10}$ metal complex, and subsequently the presence or absence of the target multiple-charged protein, is indicated by changes in optical properties, such as colorimetric assay, photoluminescence assay, or CD spectrometry analysis.

The present invention further provides kits containing various components that will allow users to perform one or more aforementioned methods of the present invention. Specifically, the present invention further provides a kit for use in detecting a multiple-charged biomolecule in a sample comprising (a) a composition comprising a charged $d^8$ or $d^{10}$ metal complex, wherein the metal complex electrostatically binds to the multiple-charged biomolecule to induce aggregation and self-assembly of the $d^8$ or $d^{10}$ metal complex through metal . . . metal interactions and $\pi$ . . . $\pi$ interactions, and (b) instructions for use.

The kits minimally include a first container that contains a solution of the charged $d^8$ or $d^{10}$ metal complex, which can be cationic or anionic, and a second container that contains an aqueous solution including at least one multiple-charged biomolecule carrying at least three net charges that are opposite in charge to that of the $d^8$ or $d^{10}$ metal complex.

EXAMPLES

The following examples are provided to illustrate embodiments of the present invention, and are by no means intended to limit the scope of the present invention. Those skilled in the art will recognize that various changes and modifications can be made in the present invention without departing from its spirit and scope.

Example 1

Representative Examples of the $d^8$ or $d^{10}$ Metal Complex

Figure 2:
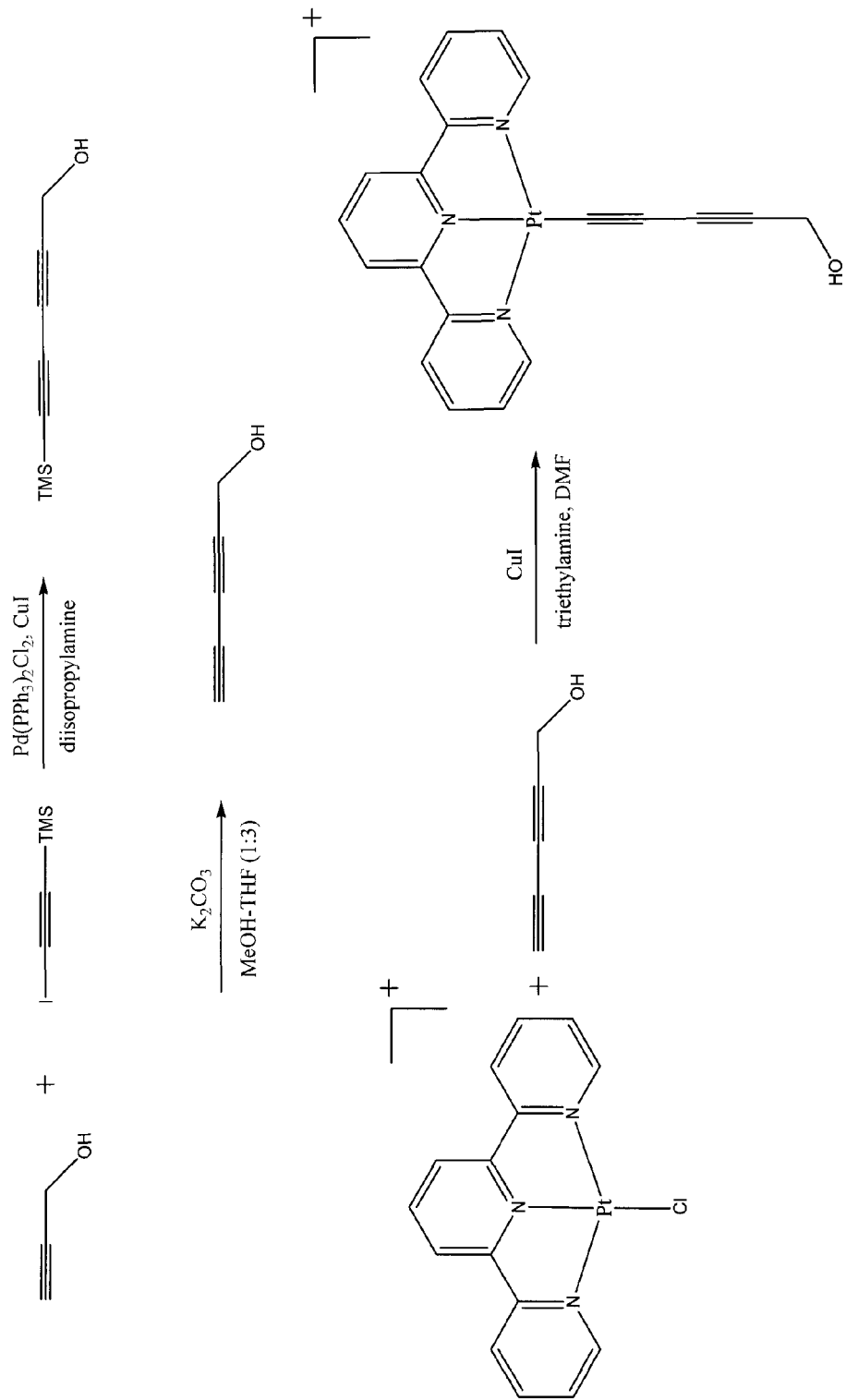
FIG. 2 shows a representative route for the synthesis of one of the illustrative examples (complex 2) shown in FIG. 1.

Two examples of the metal complexes are provided (FIG. 1). Complex 1 was prepared by existing literature methods which are known by those skilled in the art, while complex 2 was prepared via the synthetic route given in FIG. 2. Both metal complexes have certain properties that are especially suitable for the aggregation studies described in the present invention. Both complexes contain a metal center (Pt), which is a $d^8$ transition metal ion and capable of participating in metal . . . metal interactions. They also contain aromatic terpyridine ligand that can interact with each other by $\pi$ . . . $\pi$ stacking interactions.

Example 2

Binding of the $d^8$ Metal Complexes Shown in FIG. 1 to Single-Stranded DNA Studied by UV/vis Spectroscopy A polyelectrolyte, namely poly(acrylic acid) upon deprotonation, could induce aggregation and self-assembly of complex 1 in an organic solvent mixture of methanol and acetonitrile. The induced self-assembly could be interpreted based on the structural properties of the metal complex and the polyelectrolyte. The structure of the complex was nearly planar, and it carried a positive charge. On the other hand, poly (acrylic acid) upon deprotonation carried negative charges. Electrostatic interaction between the positive and negative charge brought the metal complex and the polyelectrolyte into close proximity, i.e., caused binding of the metal complexes to the polyanion. As a result, the local concentration of the metal complex increased. Equally important, the positive charge on the metal complex was balanced out by the negative charge of the polymer, and hence the repulsive force between the metal complex was largely removed. The complex could therefore easily aggregate and self-assemble together via metal . . . metal interactions, $\pi$ . . . $\pi$ interactions, or a combination of both interactions.

In an aqueous solution, the situation was slightly different, but the underlying principle remained the same, in which the hydrophobic stacking interactions of the aromatic terpyridine ligand presumably played a more important role. One additional requirement was that the metal complex must be sufficiently soluble in water. While complex 1 showed only limited solubility, complex 2 had demonstrated excellent solubility in aqueous solution. Both metal complexes were, however, easily dissolved in the concentration range suitable for the binding and aggregation studies in the present invention (around 30 μM).

Figure 3:
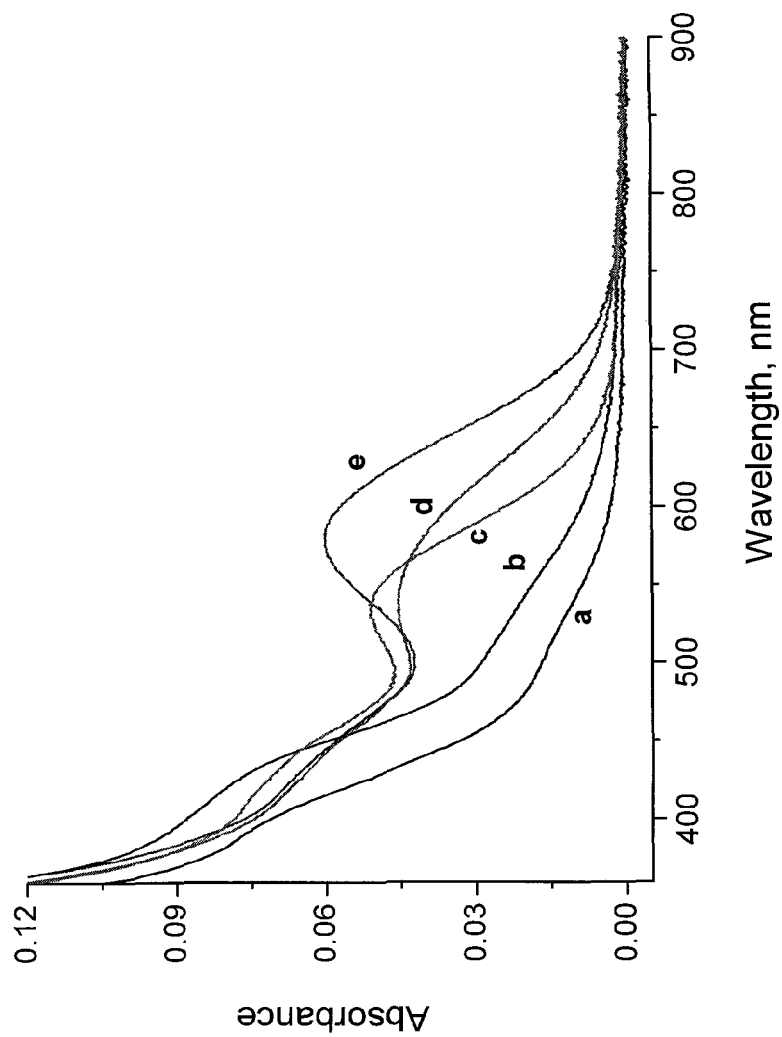
FIG. 3 shows the overlaid electronic absorption spectra of one of the representative $d^8$ metal complexes, 30 μM of complex 1 (line a), and spectral changes upon binding to 90 μM of poly(dA)$_{25}$ (line b), poly(dG)$_{25}$ (line c), poly(dC)$_{25}$ (line d), and poly(dT)$_{25}$ (line e).
Figure 4:
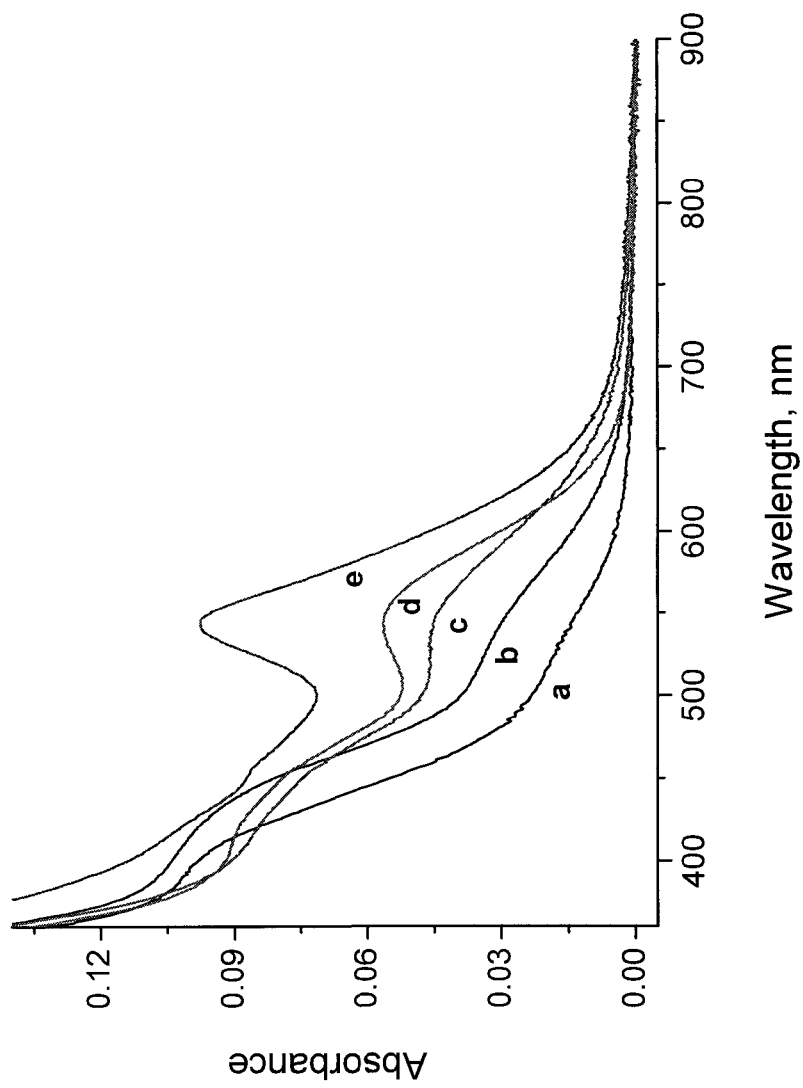
FIG. 4 shows the overlaid electronic absorption spectra of one of the representative $d^8$ metal complexes, 30 μM of complex 2 (line a), and spectral changes thereof upon binding to 90 μM of poly(dA)$_{25}$ (line b), poly(dC)$_{25}$ (line c), poly(dG)$_{25}$ (line d), and poly(dT)$_{25}$ (line e).

FIGS. 3 and 4 showed the overlaid electronic absorption spectra of complexes 1 and 2, and the corresponding spectral changes when mixed with various oligonucleotides, namely poly(dA)$_{25}$, poly(dG)$_{25}$, poly(dC)$_{25}$, and poly(dT)$_{25}$ (here and throughout the text, poly(dA)$_{25}$, poly(dG)$_{25}$, poly(dC)$_{25}$, and poly(dT)$_{25}$ represent oligonucleotides with 25 repeating units of A, G, C, and T, respectively). In an aqueous solution with 5 mM Tris pH7.5/10 mM NaCl at ambient temperature, an experimental condition used throughout the present patent, significant absorbance changes were observed. Depending on the sequence of the oligonucleotide, the absorbance changes varied quite significantly. While for poly(dT)$_{25}$, largest absorbance increases and new peak formation at about 581 nm and 544 nm were observed for complexes 1 and 2 respectively, no new peak formation and only weak absorbance changes were observed for poly(dA)$_{25}$. For poly(dC)$_{25}$ and poly(dG)$2_5$, new peak formation and moderate absorbance changes were observed.

On the basis of our previous work and other related studies, the newly formed bands of complexes 1 and 2 at longer wavelength were assigned as metal-metal-to-ligand charge transfer ("MMLCT") transitions, resulting from the aggregation of these metal complexes, through metal . . . metal interactions, π . . . . π interactions, or a combination of both interactions.

Example 3

Binding of the d$^8$ Metal Complexes Shown in FIG. 1 to Single-Stranded DNA Studied by Emission Spectroscopy Concomitant with the remarkable UV/vis changes, for some oligonucleotides, upon aggregation and self-assembly a new emission band, attributed to a MMLCT triplet origin, at about 800 nm appeared.

Figure 5:
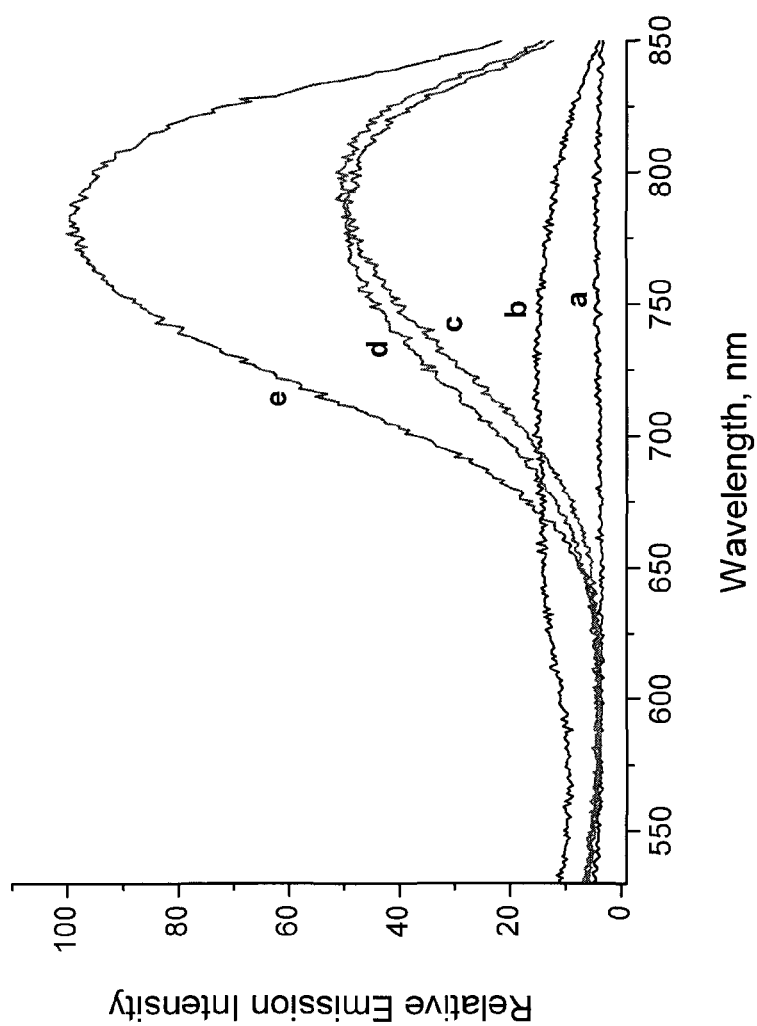
FIG. 5 shows the overlaid emission spectra of one of the representative $d^8$ metal complexes, 30 μM of complex 1 (line a), and spectral changes thereof upon binding to 90 μM of poly(dA)$_{25}$ (line b), poly(dC)$_{25}$ (line c), poly(dG)$_{25}$ (line d), and poly(dT)$_{25}$ (line e).
Figure 6:
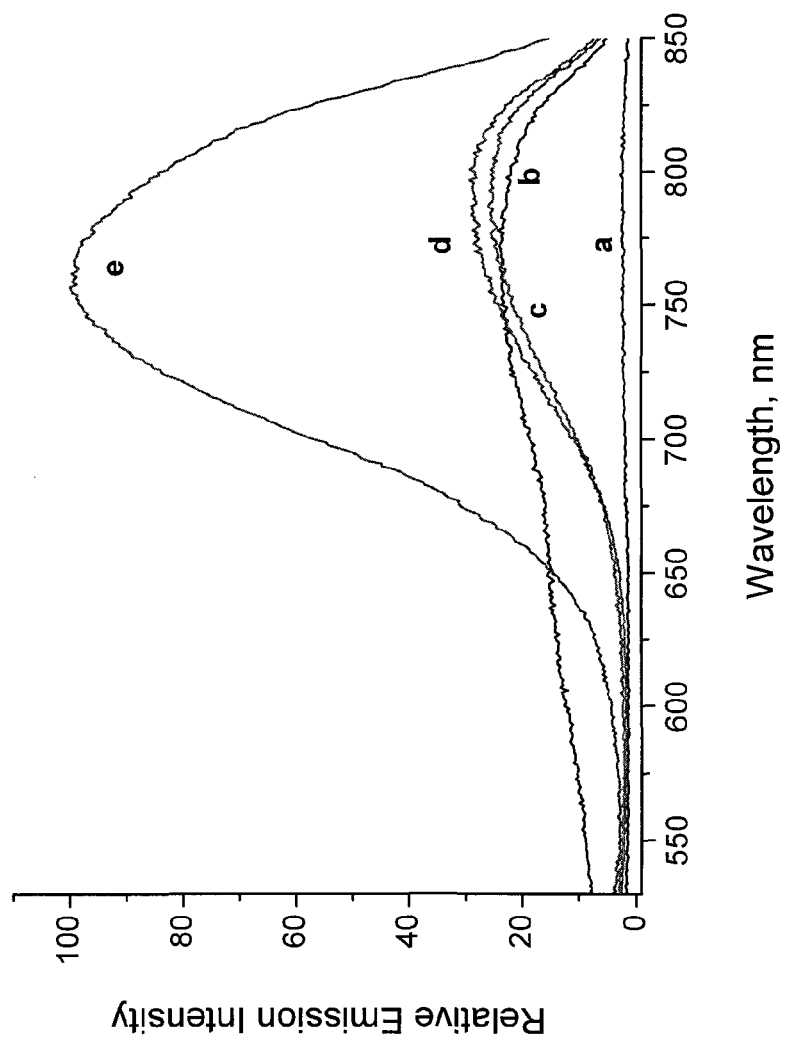
FIG. 6 shows the overlaid emission spectra of one of the representative $d^8$ metal complexes, 30 μM of complex 2 (line a), and spectral changes thereof upon binding to 90 μM of poly(dA)$_{25}$ (line b), poly(dC)$_{25}$ (line c), poly(dG)$_{25}$ (line d), and poly(dT)$_{25}$ (line e).

FIGS. 5 and 6 showed the overlaid emission spectra of complexes 1 and 2, and the corresponding emission spectra of their mixtures with various oligonucleotides (here and throughout the text, the emission spectra were not corrected for PMT response). Significant emission intensity changes for the various metal complex-oligonucleotide mixtures were observed. Complexes 1 and 2 themselves were almost non-emissive under the conditions studied. Depending on the sequence of the oligonucleotide, the intensity changes varied quite significantly. While for poly(dT)$_{25}$, largest intensity changes and a new emission band were observed at about 784 nm and 760 nm for complexes 1 and 2 respectively, a very broad and almost structureless band of weak intensity was observed for poly(dA)$_{25}$. For poly(dC)$_{25}$ and poly(dG)$_{25}$, a new band with band maximum in the range of 780-790 nm and of moderate intensity was observed.

Example 4

Figure 7:
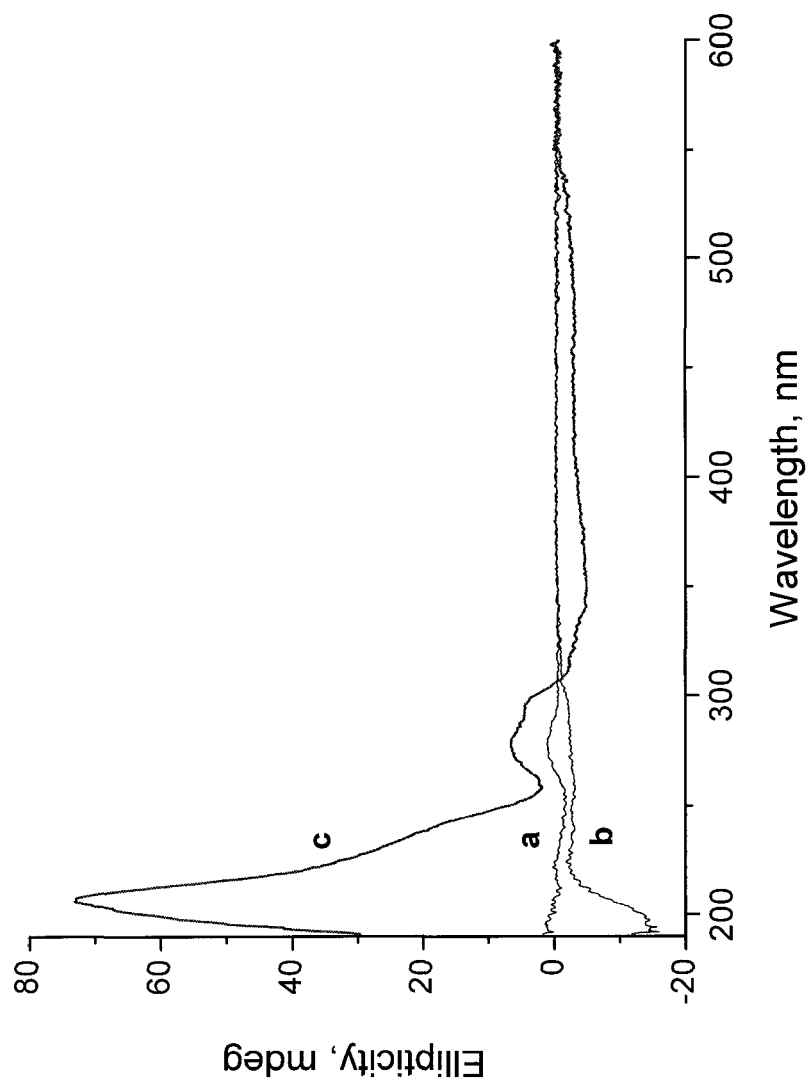
FIG. 7 shows the overlaid CD spectra of one of the representative single-stranded nucleic acids, 90 μM of poly(dT)$_{25}$ (line a), and spectral changes thereof upon binding to the $d^8$ metal complex, 30 μM, of complex 1 (line b) and complex 2 (line c).
Figure 8:
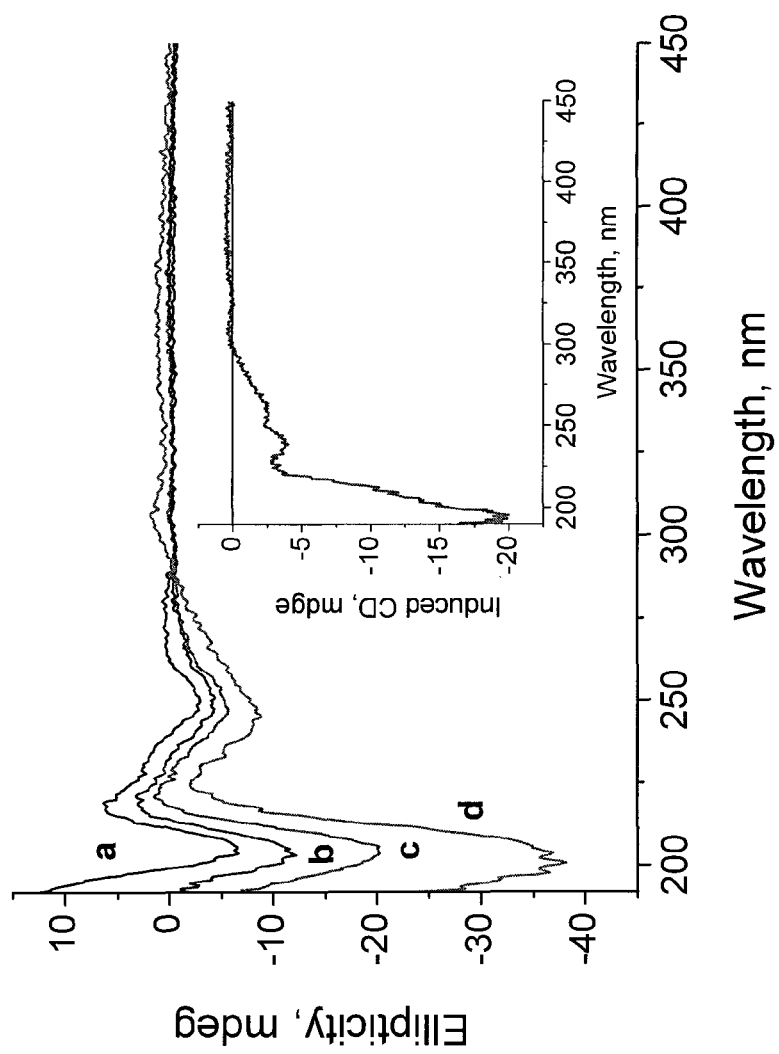
FIG. 8 shows the overlaid CD spectra of one of the representative single-stranded nucleic acids, 90 μM of poly(dA)$_{25}$ (line a), and spectral changes thereof upon binding to the $d^8$ metal complex, 30 □M of complex 1 (line b), and 30 and 60 μM of complex 2 (lines c and d). Inset Difference CD spectrum obtained by subtracting line a from line c.
Figure 9:
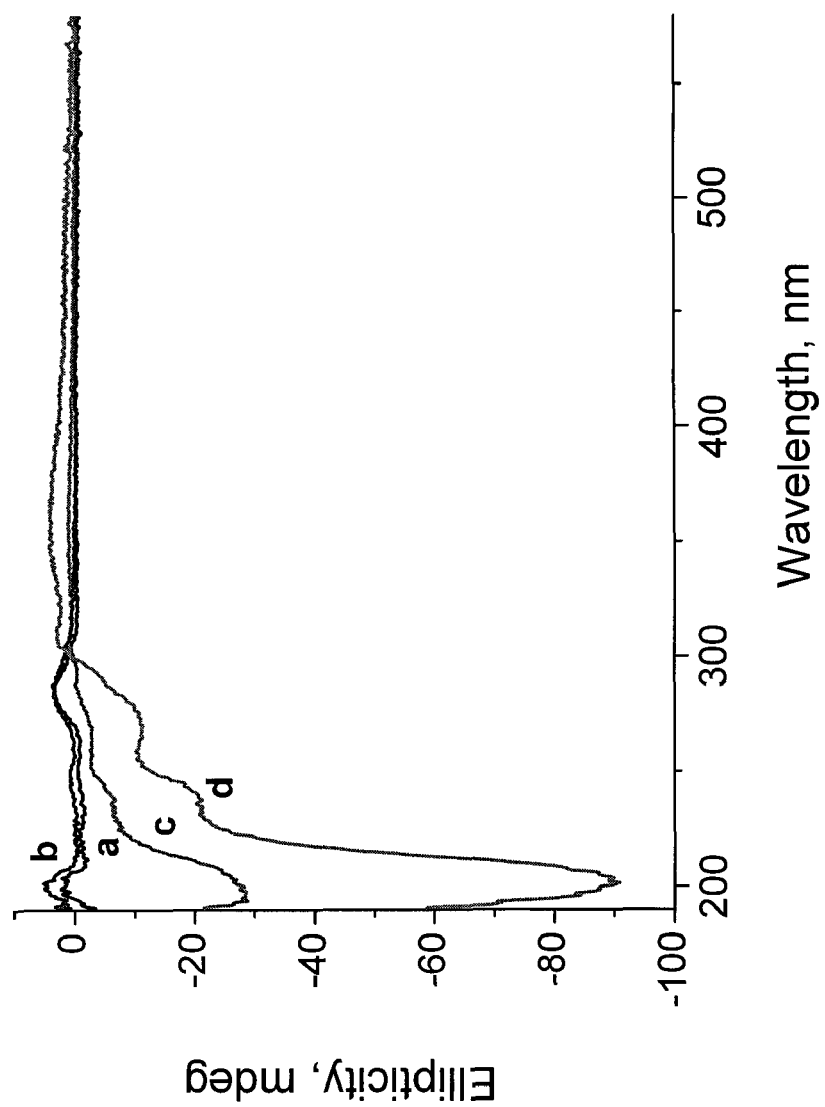
FIG. 9 shows the overlaid CD spectra of one of the representative single-stranded nucleic acids, 90 μM of poly(dC)$_{25}$ (line a), and spectral changes thereof upon binding to the $d^8$ metal complex, 30 μM of complex 1 (line b) and 30 and 45 μM of complex 2 (lines c and d).
Figure 10:
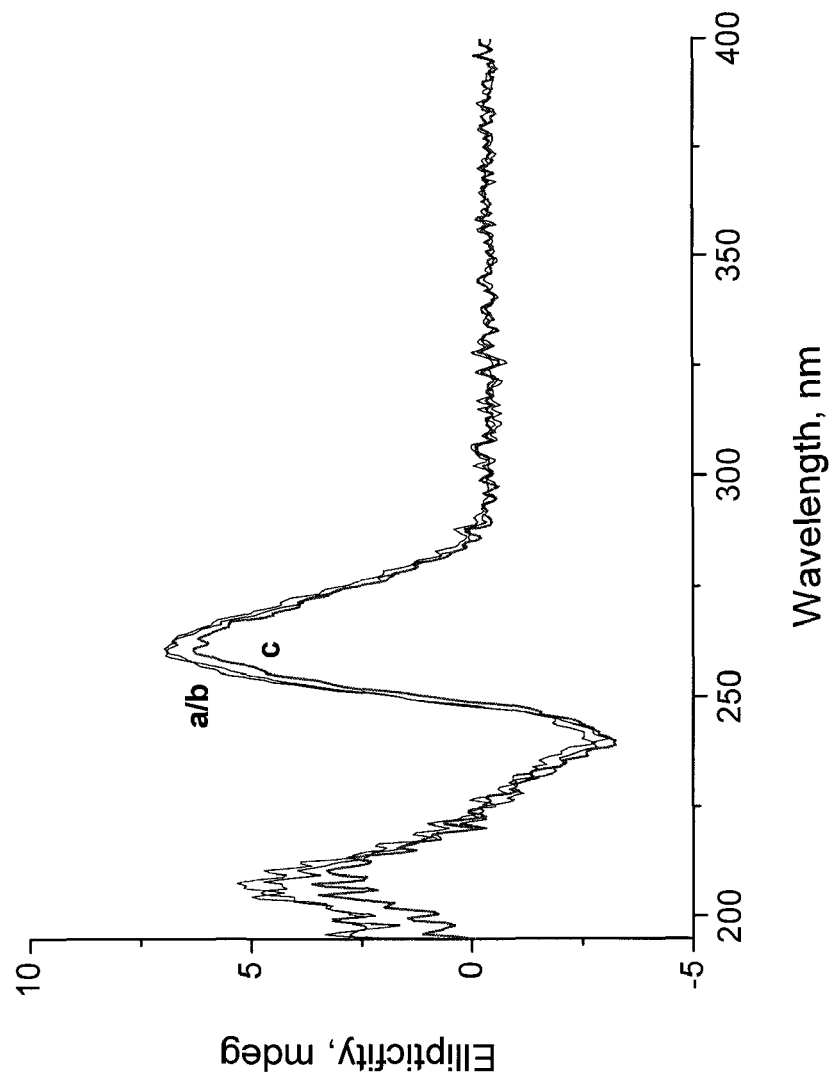
FIG. 10 shows the overlaid CD spectra of one of the representative single-stranded nucleic acids, 90 μM of poly(dG)$_{25}$ (line a), and spectral changes thereof upon binding to the $d^8$ metal complex, 30 μM of complex 1 (line b) and complex 2 (line c).

Binding of the d$^8$ Metal Complexes Shown in FIG. 1 to Single-Stranded DNA Studied by CD Spectroscopy FIGS. 7-10 showed the CD spectra of the oligonucleotides studied and the corresponding spectral changes upon mixing with complexes 1 and 2. For some oligonucleotides, significant spectral changes were observed. When complex 2 was mixed with poly(dT)$_{25}$, a broad negative band at about 307 nm to 550 nm of moderate intensity, positive bands at about 296 nm and 278 nm of moderate intensity, and a very strong positive band at about 207 nm were observed (FIG. 7). In sharp contrast, when complex 2 was mixed with poly(dC)$_{25}$, the opposite was observed, in which a broad positive band at about 315 nm to 525 nm of moderate intensity, negative bands at about 294 nm, 270 nm, and 239 nm (shoulder) of moderate intensity, and a very strong negative band at about 197 nm were observed (FIG. 9). Some mixtures showed little spectral changes, for example when mixed poly(dG)$_{25}$ with the metal complexes, only little intensity changes were observed, and no new bands were formed (FIG. 10).

Figure 17:
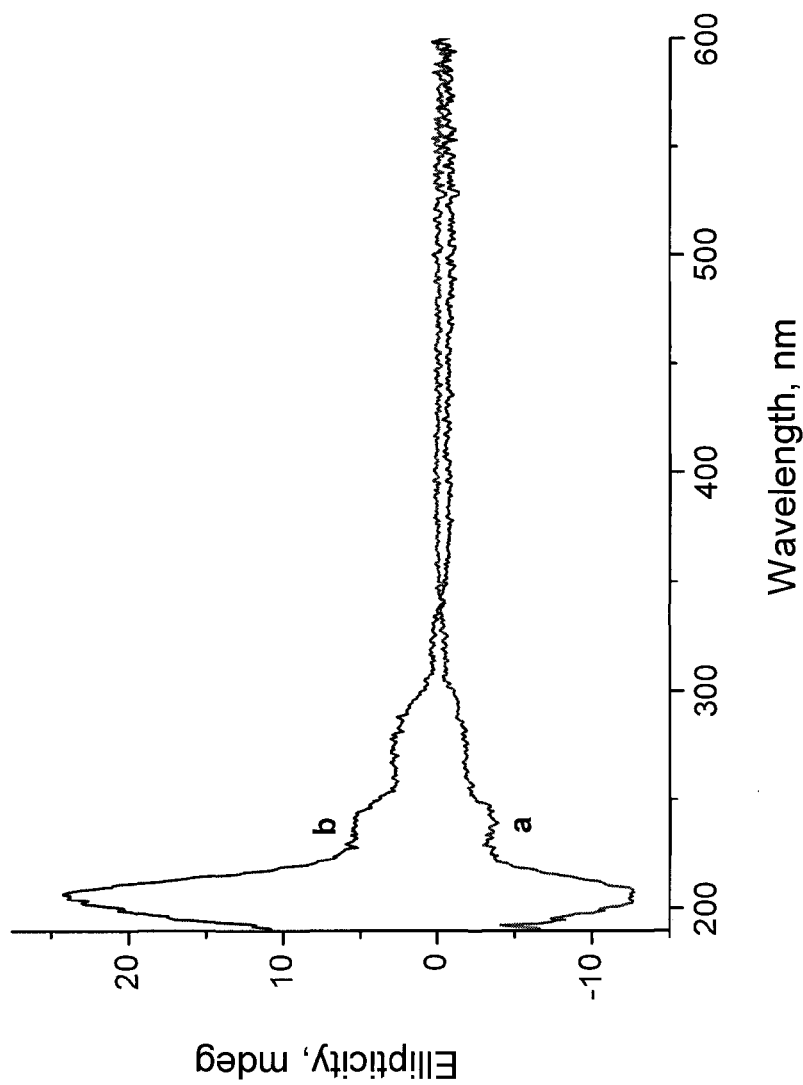
FIG. 17 shows the overlaid CD spectra of one of the representative $d^8$ metal-complexes, 30 μM of complex 2, binding to 90 μM of poly(sodium aspartate) (line a) and poly(sodium glutamate) (line b).

An achiral molecule may acquire chirality in two different ways: (i) bringing the achiral molecule into close proximity to a chiral center, in other words, by bringing an achiral chromophore into a chiral environment (e.g. phenol binding to cyclodextrin), (ii) the achiral molecule may be arranged into a helical structure and thus acquire chirality (21). Nucleic acids are well known to be inherently chiral since they contain a chiral sugar moiety. However, our results clearly show that the binding of the complexes to the nucleic acids does not always induce chirality. For example, neither the binding of complex 1 nor complex 2 to poly(dG)$_{25}$ gives any CD spectral changes, and the binding of complex 1 to poly(dC)$_{25}$ also gives rise to very little CD spectral changes. The results thus suggest that the chirality induced is not a simple consequence of bringing the platinum complexes close to the vicinity of the chiral nucleic acid, but rather more likely to be associated with the helical assembly of the platinum complexes upon binding to the anionic phosphate sites, induced by the propensity of these square-planar d$^8$ platinum(II) terpyridyl units to stack via metal . . . metal and π . . . π interactions. Supports for the helical supramolecular assembly of the complexes could be reflected by the mirror image relationship of the CD spectra obtained in the presence of poly(L-glutamate) and poly(D-glutamate) and their similarities to the CD spectra in the presence of various oligonucleotides (FIG. 17, see example 5), which could also have different helix handedness. The results thus suggest that the metal complex cations upon binding to the oligonucleotides would self-assemble into a helical supramolecular assembly of different handedness.

Figure 11:
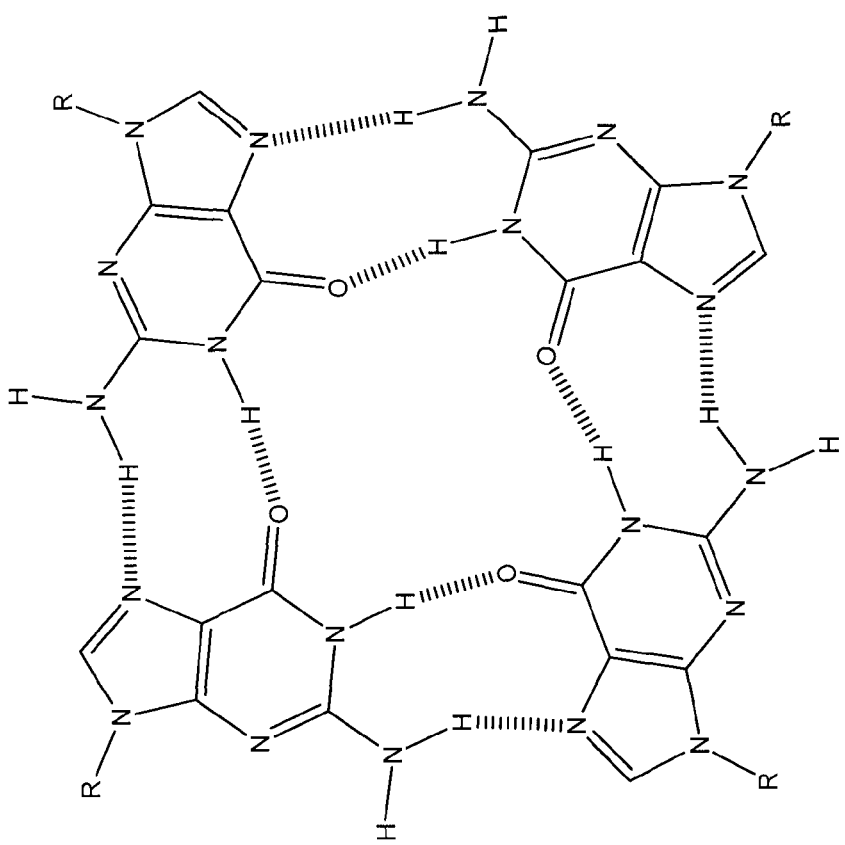
FIG. 11 shows the hydrogen bonding among four guanine bases in a G-quadruplex structure.

The changes in optical properties of the metal complexes when mixed with various oligonucleotides were apparently associated with the structural properties of the complexes, and more importantly, the primary and secondary structure of the oligonucleotides. For example, poly(dA)$_{25}$ behaved quite differently from the others, giving rise to the least extent of metal complex aggregation, which might result from the strong interaction of the nucleic base adenine with the ligand terpyridine ring via aromatic π . . . π interactions, and interfered with the self-assembly process of the metal complex. Interestingly, the other purine base, the guanine base of dG, induced better metal complex aggregation, probably because poly(dG)$_{25}$ formed a quite unique secondary structure called G-quadruplex in an aqueous solution, in which the guanine base hydrogen-bonded and stacked with each other (FIG. 11), and as a result, protected from the π . . . π interactions with the metal complex. The thymine base of dT was shown to be unable to interact with each other through π . . . π stacking interactions, and its relative hydrophilic nature as well as the presence of a bulky methyl group presumably also prevented its π . . . π interactions with the metal complex, and as a result, poly(dT)$_{25}$ induced the largest degree of metal complex aggregation and self-assembly.

Example 5

Figure 12:
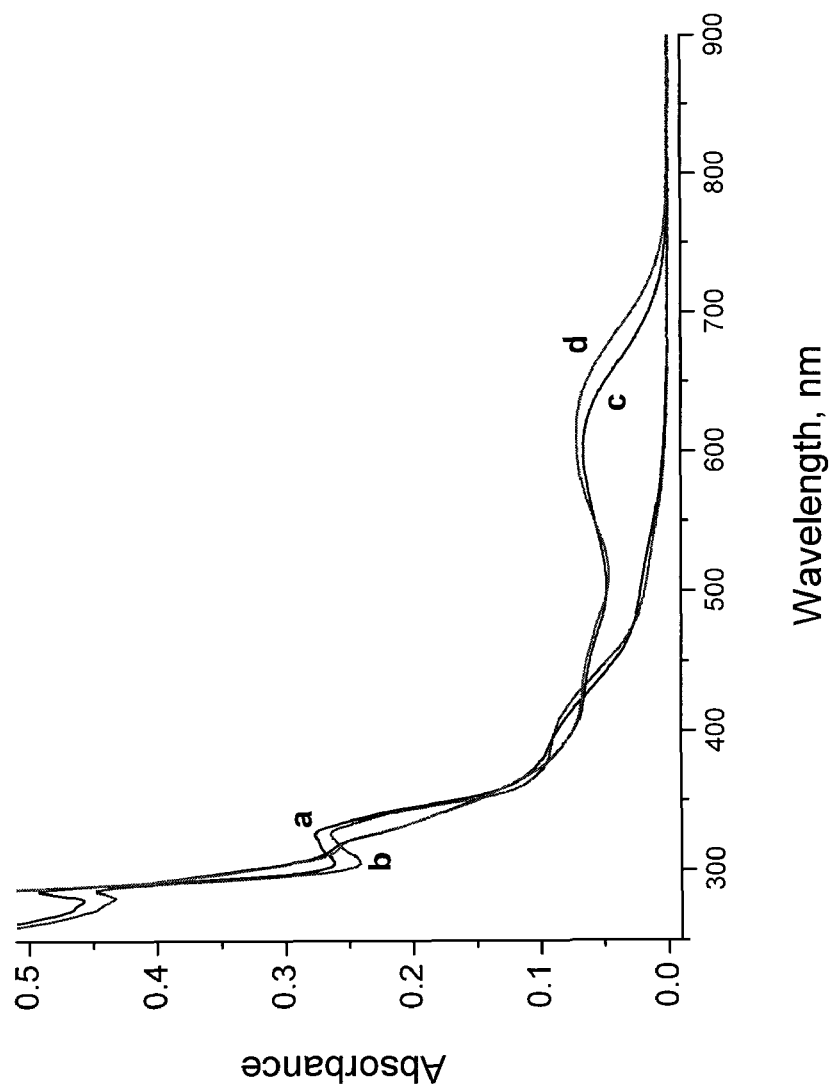
FIG. 12 shows the overlaid electronic absorption spectra of the representative $d^8$ metal complexes, 30 μM of complexes 1 (line a) and 2 (line b), and spectral changes thereof upon binding to 90 μM of polyU (lines c and d for complexes 1 and 2 respectively).
Figure 13:
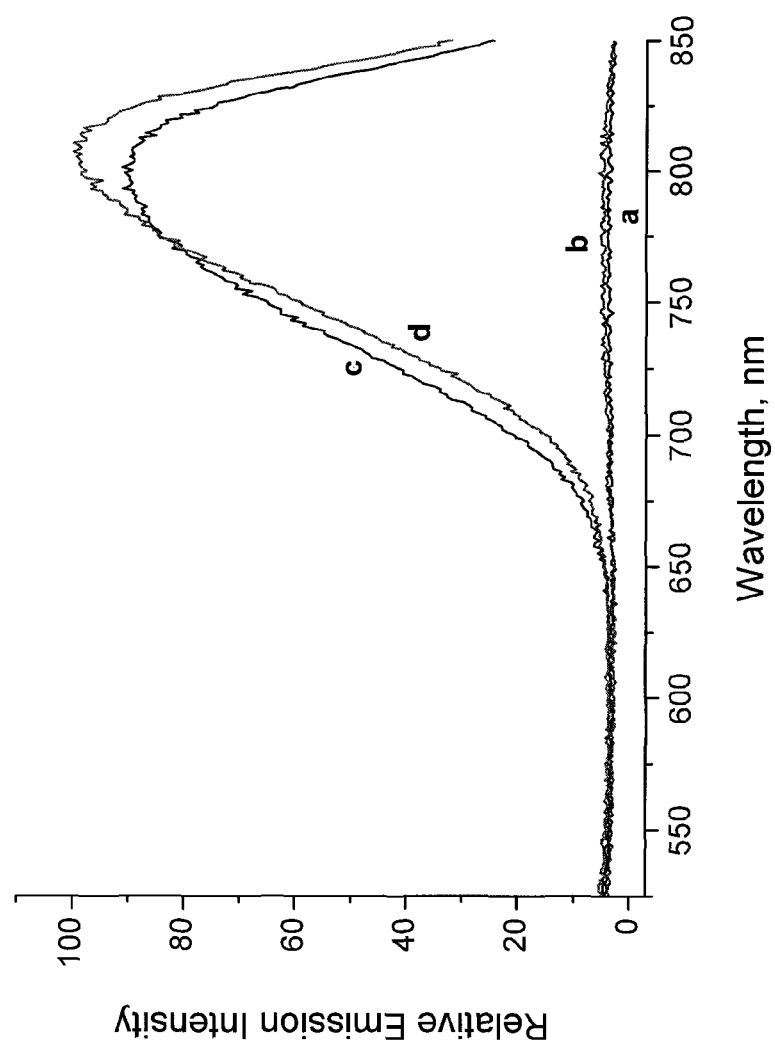
FIG. 13 shows the overlaid emission spectra of the representative $d^8$ metal complexes, 30 μM of complexes 1 (line a) and 2 (line b), and spectral changes thereof upon binding to 90 μM of polyU (lines c and d for complexes 1 and 2 respectively).
Figure 14:
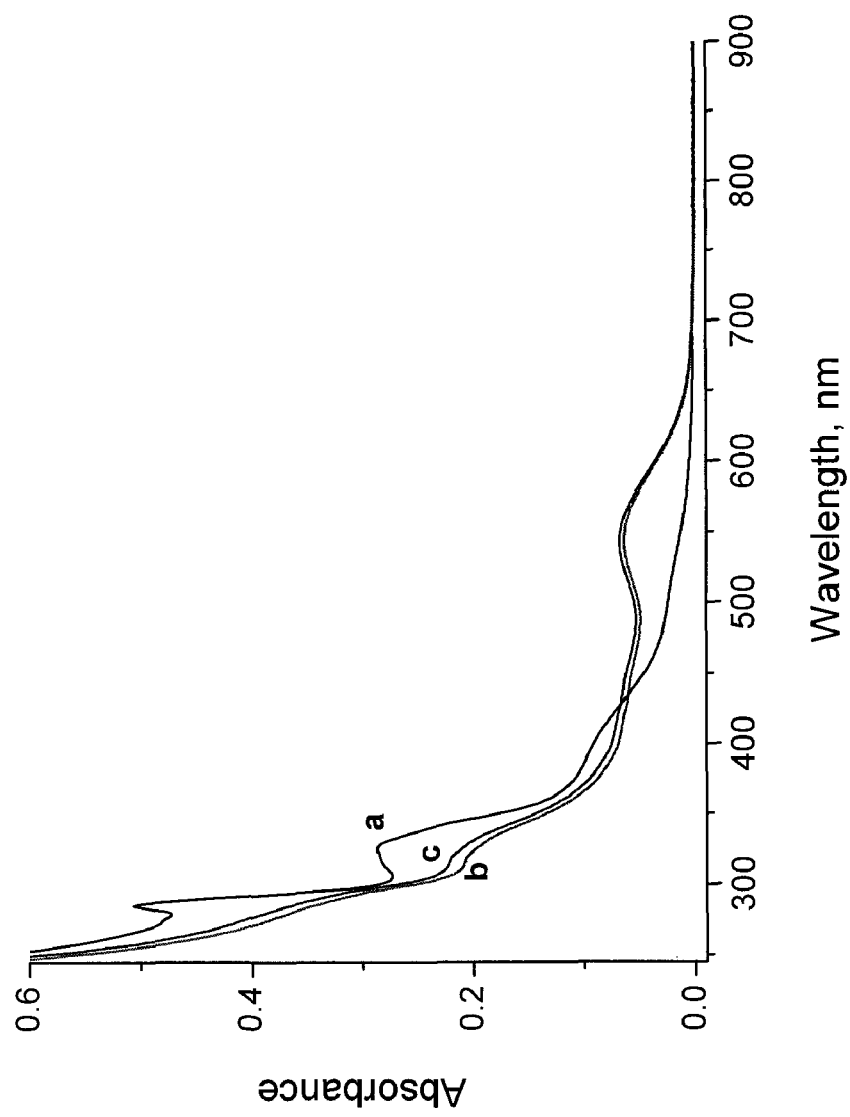
FIG. 14 shows the overlaid electronic absorption spectra of one of the representative $d^8$ metal complexes, 30 μM of complex 1 (line a), and spectral changes thereof upon binding to 90 μM of poly(sodium aspartate) (line b) and poly(sodium glutamate) (line c).
Figure 15:
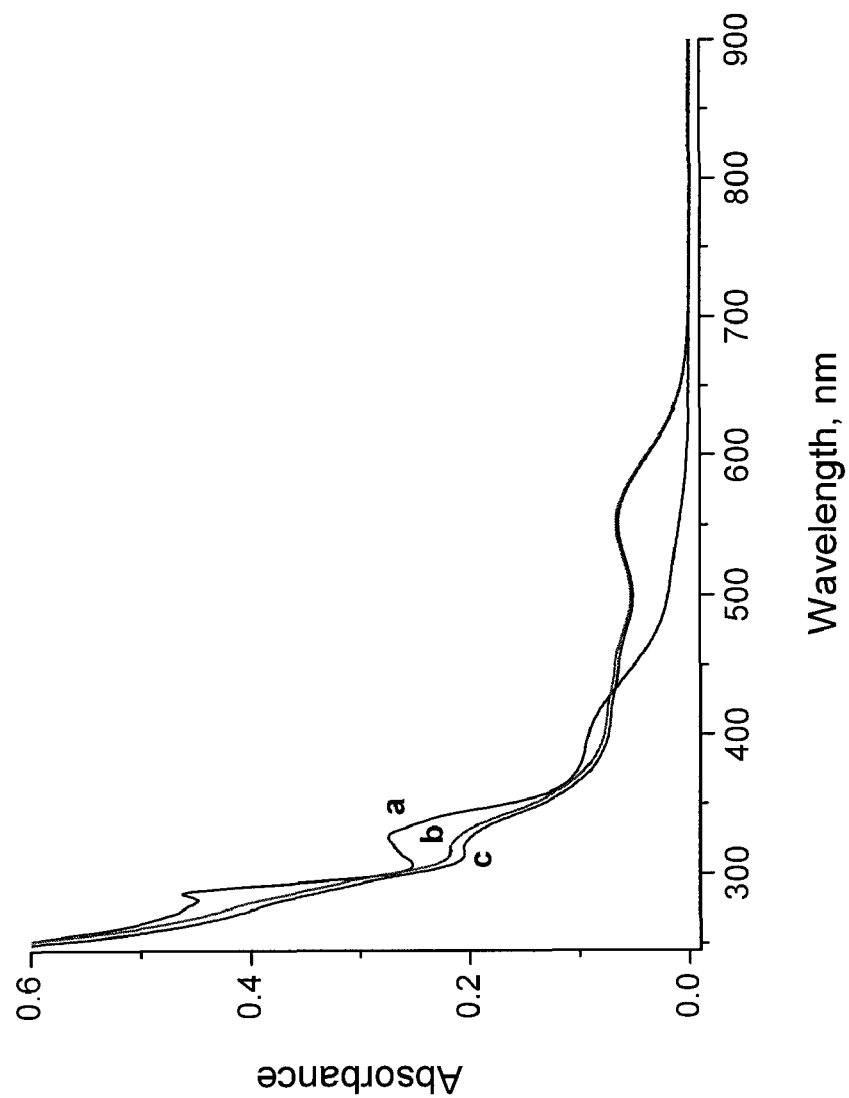
FIG. 15 shows the overlaid electronic absorption spectra of one of the representative $d^8$ metal complexes, 30 μM of complex 2 (line a), and spectral changes thereof upon binding to 90 μM of poly(sodium aspartate) (line b) and poly(sodium glutamate) (line c).
Figure 16:
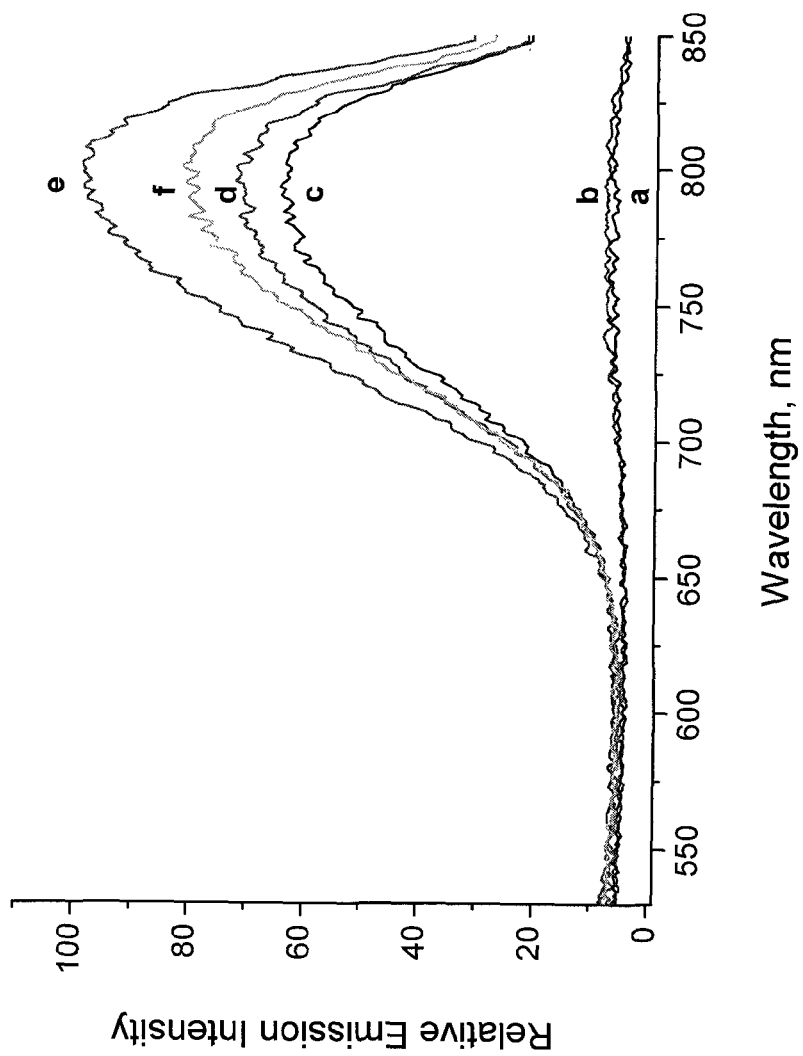
FIG. 16 shows the overlaid emission spectra of the representative $d^8$ metal complexes, 30 μM of complexes 1 (line a) and 2 (line b), and spectral changes thereof upon binding to 90 μM of poly(sodium aspartate) (lines c and d for complexes 1 and 2 respectively) and poly(sodium glutamate) (lines e and f for complexes 1 and 2 respectively).

Binding of the $d^8$ Metal Complexes Shown In FIG. 1 to an RNA Molecule (polyU), Poly(sodium aspartate), and Poly(sodium glutamate) Studied by UV/vis, Emission, and CD Spectroscopy FIGS. 12 and 13 showed the UV/vis and emission spectral changes upon mixing of complexes 1 or 2 with polyU. FIGS. 14-17 showed the UV/vis, emission, and CD spectral changes upon mixing of complexes 1 or 2 with poly(sodium aspartate) and poly(sodium glutamate). These biomolecules all carried multiple negative charges in an aqueous solution at near neutral pH, thus just like binding to single-stranded nucleic acid, when mixed with the positively charged metal complex, induced aggregation and self-assembly of complexes 1 and 2 would occur, leading to subsequent remarkable spectroscopic property changes.

Example 6

Figure 18:
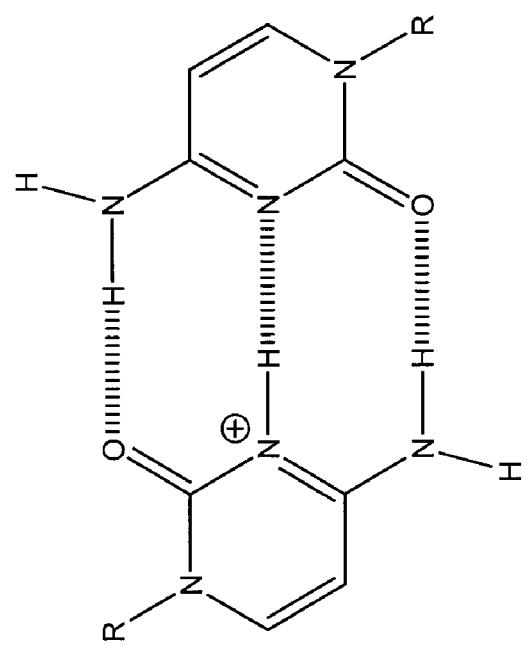
FIG. 18 shows the hydrogen bonding in cytosine-protonated cytosine (C—C$^+$) base pair.
Figure 19:
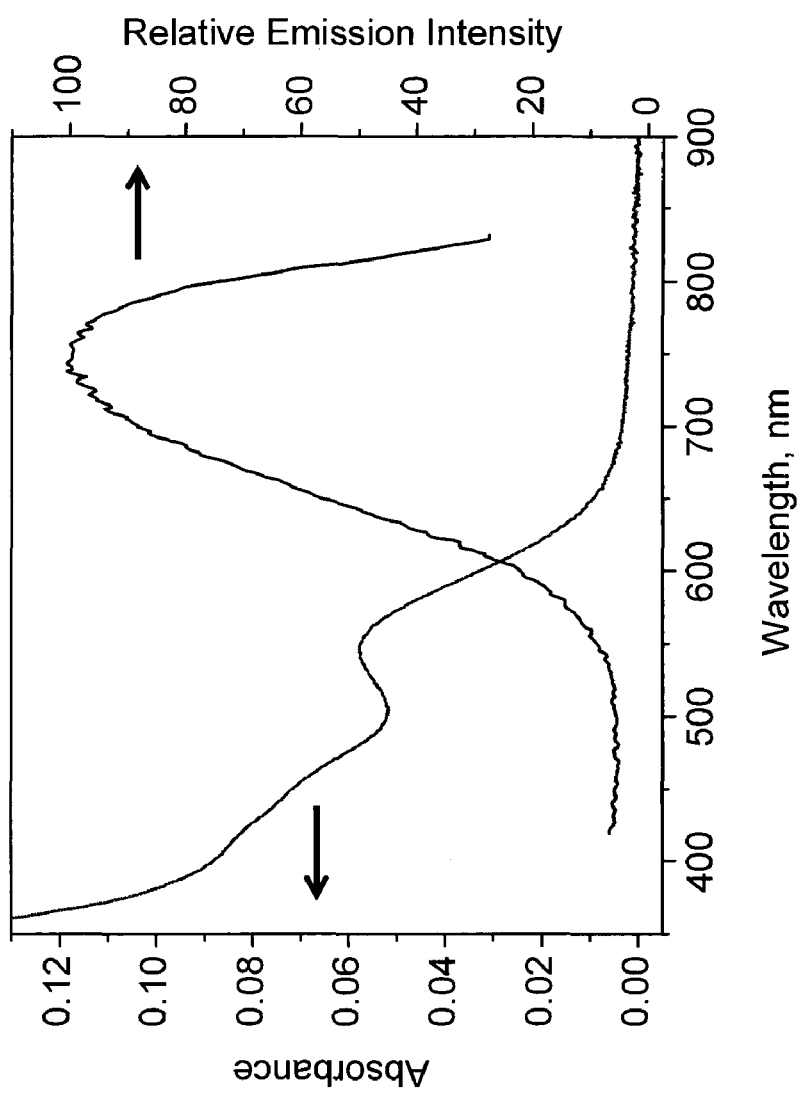
FIG. 19 shows the overlaid UV-vis absorption and emission spectra of 90 μM of poly(dC)$_{25}$ 30 μM of complex 2. Medium: 5 mM HOAc—NaOAc, 10 mM NaCl, pH 5.0.
Figure 20:
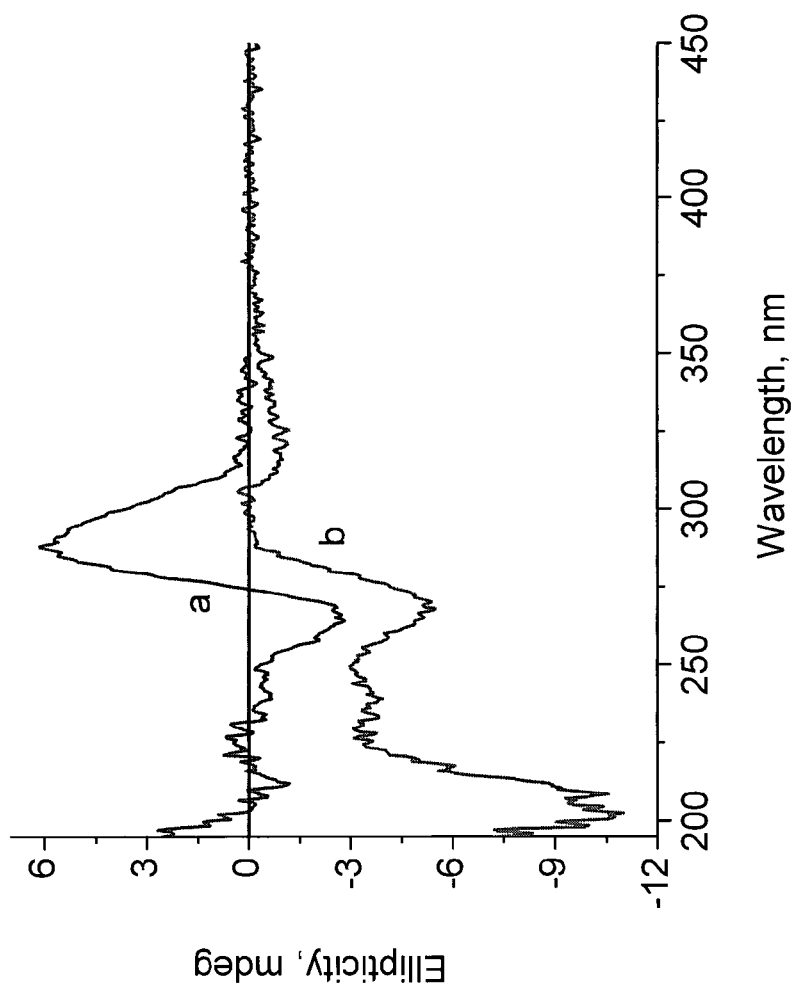
FIG. 20 shows the overlaid CD spectra of poly(dC)$_{25}$ (line a), and its binding with complex 2 (line b). Medium: 5 mM HOAc-NaOAc, 10 mM NaCl, pH 5.0.

Binding of the $d^8$ Metal Complex 2 shown In FIG. 1 to i-Motif DNA Structure Studied by UV/vis, Emission, And CD Spectroscopy Although poly(dC) is known to adopt a helical conformation under basic conditions, under acidic conditions, poly(dC) forms the very unique i-motif structure, as a result of the C—$C^+$ (cytosine—protonated cytosine) base paring (FIG. 18). At pH 5.0, our results show improved self-assembly of complex 2 when mixed with poly(dC)$_{25}$, as revealed by the enhancement of the MMLCT bands in both the UV-vis and the emission spectra (FIG. 19). However, the CD spectrum induced by metal complex binding is found to be quite different from the helical assembly obtained previously, and also different from the CD signatures of the i-motif structure (FIG. 20), that is initially formed before metal complex binding. The very compact i-motif structure appears to facilitate the self-assembly of the complex cations, albeit different from the helical assembly as revealed by the CD.

Example 7

Figure 21:
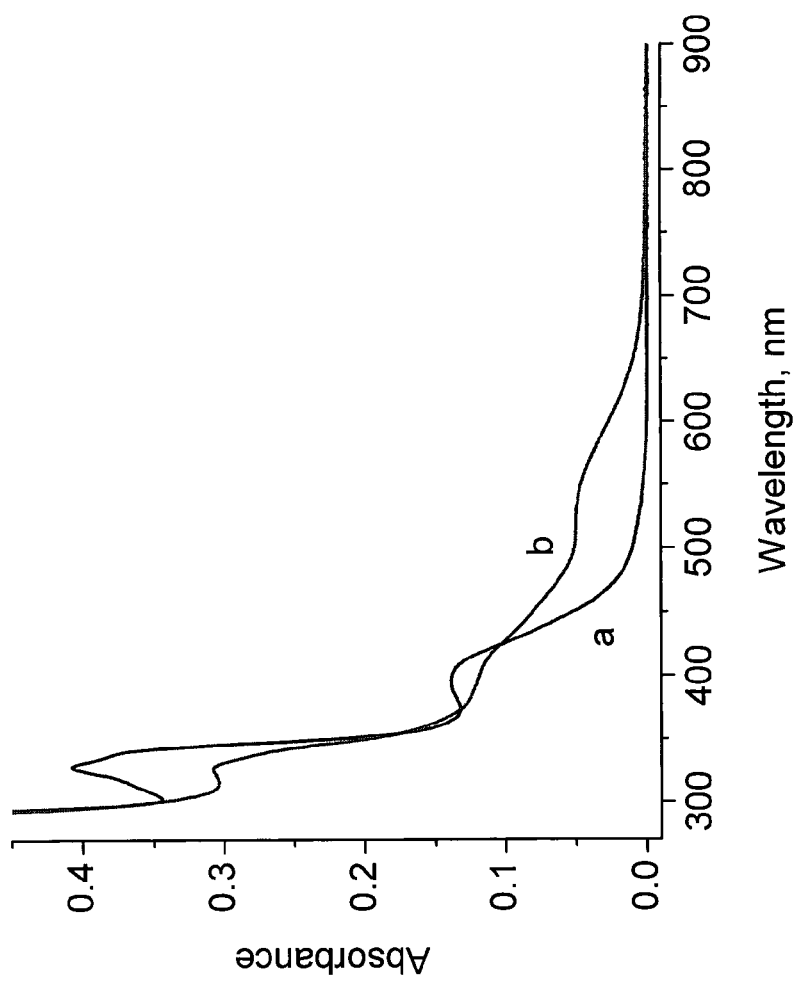
FIG. 21 shows the overlaid UV-vis absorption spectra of 30 μM of complex 2 (line a), and its binding to 90 μM of poly (dA)$_{25}$ (line b). Medium: 80% aqueous buffer (5 mM Tris-HCl, 10 mM NaCl, pH 7.5)+20% CH$_3$CN.
Figure 22:
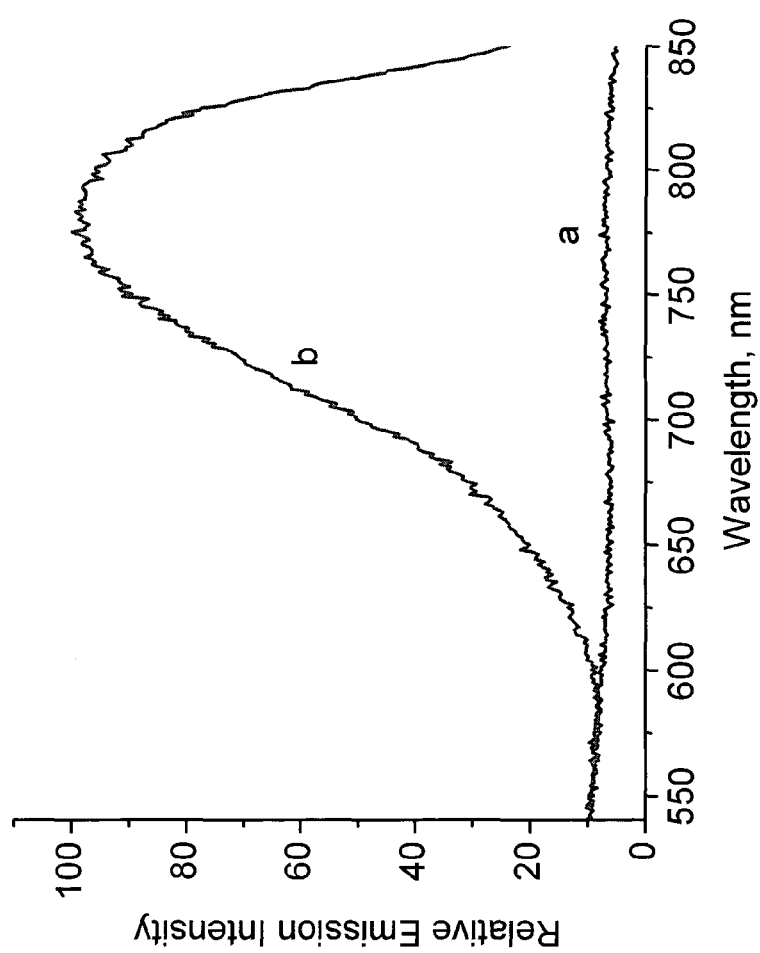
FIG. 22 shows the overlaid emission spectra of 30 μM of complex 2 (line a), and its binding to 90 μM of poly(dA)$_{25}$ (line b). Medium: 80% aqueous buffer (5 mM Tris-HCl, 10 mM NaCl, pH 7.5)+20% CH$_3$CN.

Binding of the $d^8$ Metal Complex 2 Shown in FIG. 1 to Single-Stranded DNA Studied by UV/vis, Emission, and CD Spectroscopy, the Influence of Organic Solvents The effect of addition of an organic solvent to the complex self-assembly properties was also studied, since it is well known that addition of an organic solvent could reduce the hydrophobic interactions in an aqueous medium, and in this case reduce the $\pi \ldots \pi$ interactions with the oligo that compete with the formation of complex self-assembly. In the binding studies of complex 2 with poly(dA)$_{25}$, addition of 20% $CH_3CN$ completely eliminates the complex monomer emission, and the UV-vis and emission spectral changes also indicate rather good self-assembly of the complex (FIGS. 21 and 22). The results show that the increase in organic solvent content reduces the $\pi \ldots \pi$ hydrophobic stacking interactions between the metal complex and the nucleic acid base that give rise to complex monomer emission. However, weaker CD signals are observed, indicating a reduced helicity under such conditions. Addition of 20% trifluoroethanol (TFE) also gives similar results. With poly(dT)$_{25}$, in the presence of 20% TFE, complex 2 gives nicely defined helical assembly, as revealed from the UV-vis, emission and CD measurements, albeit a bit less strongly than in aqueous buffer.

Figure 23:
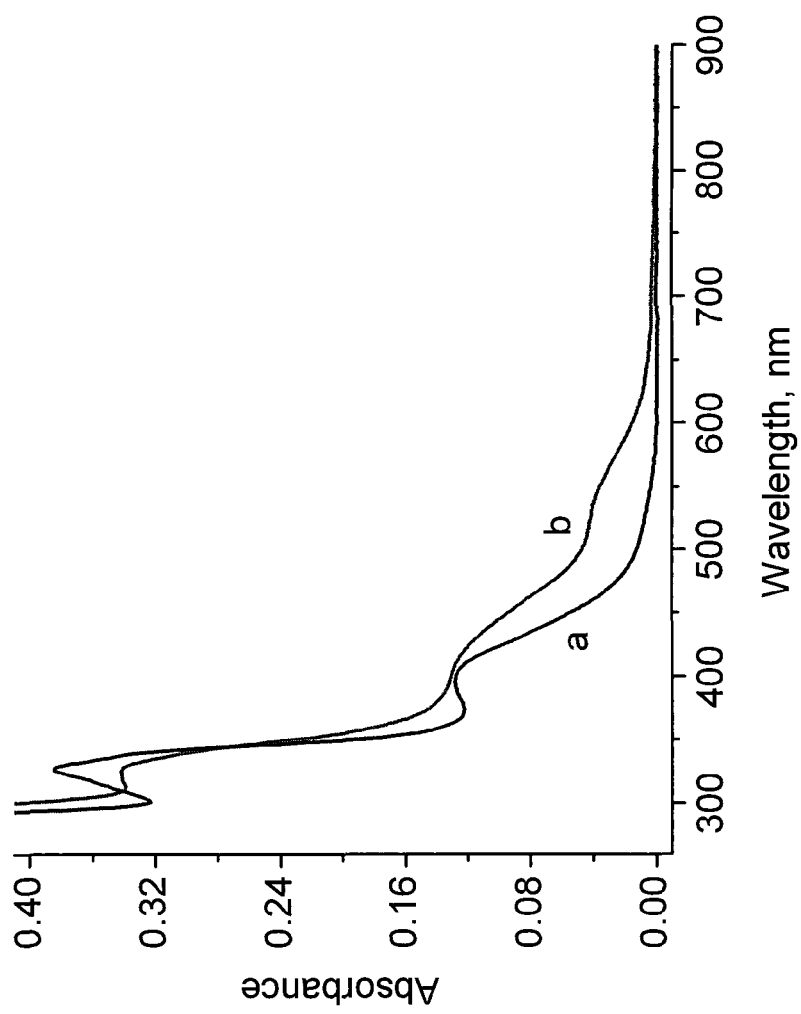
FIG. 23 shows the overlaid UV-vis absorption spectra of 30 μM of complex 2 (line a), and its binding to 90 μM of the oligonucleotide (CAT TAC TGG ATC TAT CAA CAG GAG) (line b). Medium: 80% aqueous buffer (5 mM Tris-HCl, 10 mM NaCl, pH 7.5)+20% TFE.
Figure 24:
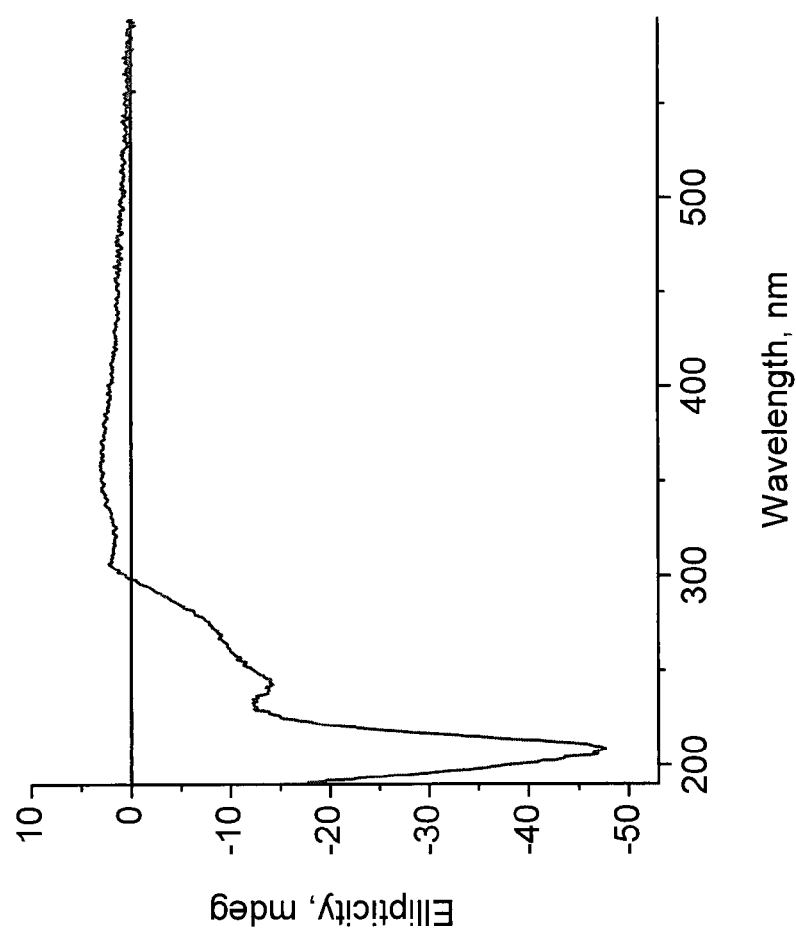
FIG. 24 shows the CD spectrum of 30 μM of complex 2 binding to 90 μM (total base concentration) of oligonucleotide (CAT TAC TGG ATC TAT CAA CAG GAG). Medium: 80% aqueous buffer (5 mM Tris-HCl, 10 mM NaCl, pH 7.5)+20% TFE.

An oligonucleotide sequence containing all four bases was randomly selected. The sequence is CAT TAC TGG ATC TAT CAA CAG GAG (a standard vector primer). In pure buffer, its mixture with complex 2 shows only weakly induced self-assembly of the complex, presumably due to the hydrophobic interactions between the nucleic acid bases and the complex cation, and possibly some ill-defined secondary structures of the oligonucleotide. However, when 20% TFE was added, both the UV-vis and emission spectra indicate good self-assembly of the metal complex (FIG. 23), and a strong CD signal indicative of an assembly that is strongly helical in nature is observed (FIG. 24).

Based on the observation of different trends with the four different nucleobases, it seems that the subtle competition between the hydrophobic $\pi$ stacking interactions with DNA and the metal-metal interaction assisted self-assembly of the platinum(II) complexes plays an important role in governing the delicate balance between them.

Example 8

Figure 25:
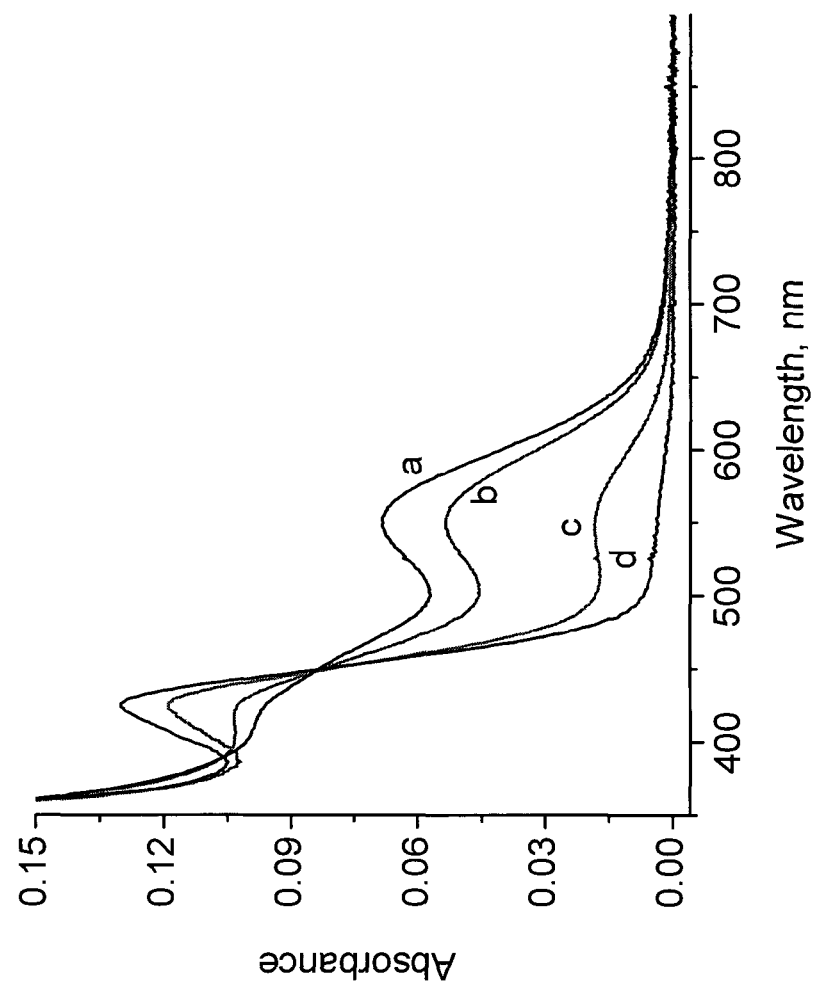
FIG. 25 shows the overlaid UV-vis absorption spectra of 30 μM of complex 2 binding to: 45 μM of poly(dA)$_{25}$+45 μM of poly(dT)$_{25}$ (line a); 90 μM of poly(dA)$_{25}$+90 μM of poly(dT)$_{25}$ (line b); 180 μM of poly(dA)$_{25}$+180 μM of poly (dT)$_{25}$ (line c); 270 μM of poly(dA)$_{25}$+270 μM of poly(dT)$_{25}$ (line d). Medium: 5 mM Tris-HCl, 10 mM NaCl, pH 7.5.
Figure 26:
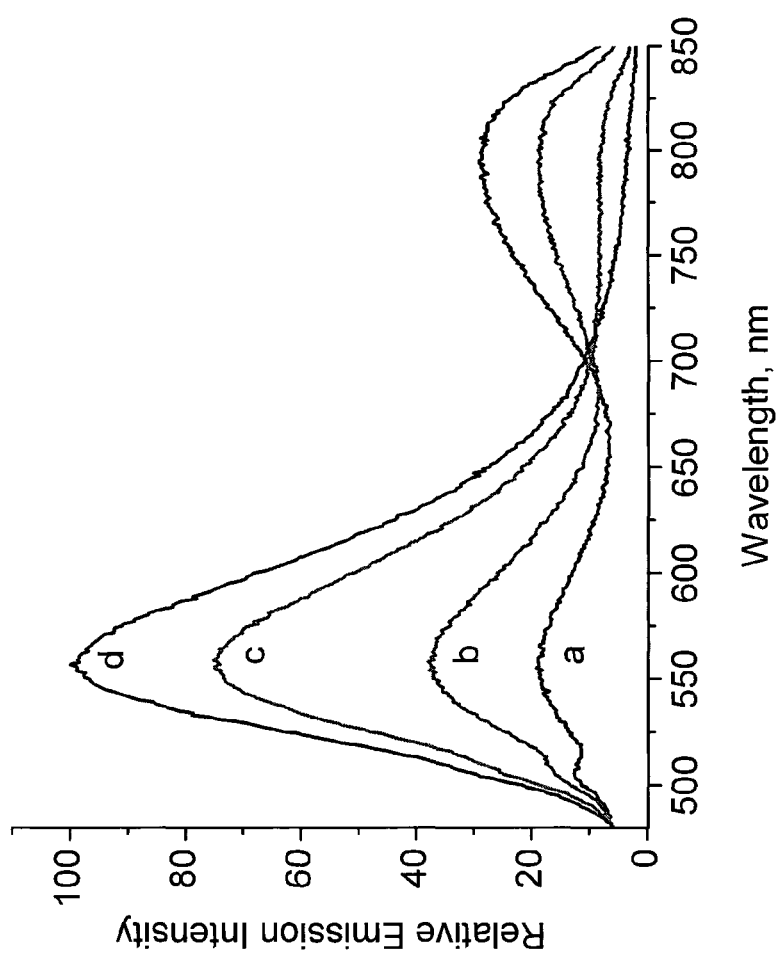
FIG. 26 shows the overlaid emission spectra of 30 μM of complex 2 binding to: 45 μM of poly(dA)$_{25}$+45 μM of poly (dT)$_{25}$ (line a); 90 μM of poly(dA)$_{25}$+90 μM of poly(dT)$_{25}$ (line b); 180 μM of poly(dA)$_{25}$+180 μM of poly(dT)$_{25}$ (line c); 270 μM of poly(dA)$_{25}$+270 μM of poly(dT)$_{25}$ (line d). Medium: 5 mM Tris-HCl, 10 mM NaCl, pH 7.5.

Binding of the $d^8$ Metal Complex 2 Shown in FIG. 1 to Double-Stranded DNA Studied by UV/vis, Emission, and CD Spectroscopy We have also extended our studies to double-stranded DNA. Preliminary studies show that upon addition of 30 µM of complex 2 to a poly(dA)$_{25}$-poly(dT)$_{25}$ duplex, prepared by mixing equal amounts (45 µM, base concentration) of the respective poly(dA)$_{25}$ and poly(dT)$_{25}$, both the UV-vis and emission spectra show pronounced MMLCT bands, and changes in the CD signal typical of the complex helical assembly are also observed. With an increasing amount of the duplex DNA, the MMLCT absorption band gradually disappears, and a new band at 425 nm emerges in the UV-vis spectra (FIG. 25). Concomitant with the UV-vis spectral changes, the emission band at around 800 nm gradually disappears, and a new strong emission band at around 557 nm emerges (FIG. 26). In addition, at high duplex concentration {270 µM poly(dA)$_{25}$+270 µM poly(dT)$_{25}$, base concentration}, addition of 30 µM of complex 2 causes little CD spectral changes. Since the square planar platinum terpyridyl type complexes are well known duplex DNA intercalators, the results suggest that at low duplex concentrations, most of the complexes are bound to the anionic phosphate groups on the DNA via electrostatic interactions, leading to a helical self-assembly, while at high concentrations of the duplex DNA, the majority of the complexes would intercalate into the duplex and therefore self-assembly of the complexes is not observed. The shift of the absorption and emission bands to a shorter wavelength of 425 nm and 557 nm respectively, strongly indicates that the complex cations are in a very different environment, presumably stacked between the nucleotide base pairs in an intercalative manner.

REFERENCES

The following patents, patent applications, and articles (or any other cited references throughout the application) are incorporated herein by reference.
1. U.S. Pat. No. 5,985,567, issued Nov. 16, 1999 (Rampal).
2. U.S. Pat. No. 6,132,972, issued Oct. 17, 2000 (Shigemori et al.).
3. U.S. Publication Application No. U.S.20050059042, published Mar. 17, 2005 (Rothberg et al.).
4. U.S. Publication Application No. U.S.20040219556, published Nov. 4, 2004 (Bazan et al.).
5. U.S. Publication Application No. U.S.20040033518, published Feb. 19, 2004 (Wittwer et al.).
6. U.S. Publication Application No. US20050048485, published Mar. 3, 2005 (Kurane et al.).
7. U.S. Publication Application No. US20010046670, published Nov. 29, 2001 (Brookes).
8. PCT International Publication No. WO2004111602, published Dec. 23, 2004 (Rothberg et al.).

9. PCT International Publication No. WO03091408, published Nov. 6, 2003 (Wittwer et al.).
10. PCT International Publication No. WO9846790, published Oct. 22, 1998 (Harbron).
11. PCT International Publication No. WO9942616, published Aug. 26, 1999 (Patel et al.).
12. Canadian Patent Application No. CA2489922, filed Jun. 20, 2003 (Gaylord, B. and Bazan, G.).
13. British Patent No. GB2318791, issued May 6, 1998 (Charles).
14. Japanese Patent No. JP11151100, issued Jun. 8, 1999 (Shigemori et al.).
15. Japanese Patent No. JP61219400, issued Sep. 29, 1986 (Yokota et al.).
16. KOKAI Open Application No. JP2005000088, published Jan. 6, 2005 (Shigemori et al.).
17. Adamovich et al., "High Efficiency Single Dopant White Electrophosphorescent Light Emitting Diodes", New Journal of Chemistry, 2002, 26, 1171-1178.
18. Backburn et al. ed., "Nucleic Acids in Chemistry and Biology", Oxford University Press, Oxford, 1996.
19. Bloomfield et al., "Nucleic Acids: Structures, Properties, and Functions", University Science Books, California, 2000.
20. Creighton, "Proteins: Structure and Molecular Properties", W. H. Freeman and Company, New York, 1993.
21 Fasman ed., "Circular Dichroism and the Conformational Analysis of Biomolecules", Plenum Press, New York, 1996.
22. Gaylord et al., "DNA Detection Using Water-Soluble Conjugated Polymers and Peptide Nucleic Acid Probes", Proceedings of the National Academy of Sciences of the United States of America, 2002, 99, 10954-10957.
23. Goshe et al., "Supramolecular Recognition. Terpyridyl Palladium and Platinum Molecular Clefts and Their Association with Planar Platinum Complexes", Journal of the American Chemical Society, 2003, 125, 444-451.
24. Li et al., "Label-Free Colorimetric Detection of Specific Sequence in Genomic DNA by the Polymerase Chain Reaction", Journal of the American Chemical Society, 2004, 126, 10958-10961.
25. Yam et al., "Luminescent Platinum(II) Terpyridyl Complexes: Effect of Counter Ions on Solvent-Induced Aggregation and Color Changes", Chemistry—A European Journal, 2005, 11, 4535-4543
26. Yam et al., "Solvent-Induced Aggregation through Metal . . . Metal/π . . . π Interactions: Large Solvatochromism of Luminescent Organoplatinum(II) Terpyridyl Complexes", Journal of the American Chemical Society, 2002, 124, 6506-6507.
27. Yam et al., "Synthesis, Luminescence, Electrochemistry, and Ion-Binding Studies of Platinum(II) Terpyridyl Acetylide Complexes", Organometallics, 2001, 20, 4476-4482.
28. Yu et al., "Polymer-Induced Self-Assembly of Alkynylplatinum(II) Terpyridyl Complexes by Metal. Metal/π . . . π Interactions", Angewandte Chemie International Edition, 2005, 44, 791-794.
29. Yu et al., "Single-Stranded Nucleic Acid-Induced Helical Self-Assembly of Alkynylplatinum(II) Terpyridyl Complexes." Proceedings of the National Academy of Sciences of the United States of America, 2006, 103, 19652-19657.

What is claimed is:

1. A composition for detecting a multiply-charged biomolecule comprising a charged $d^8$ or $d^{10}$ metal complex, wherein the metal complex electrostatically binds to the multiple-charged biomolecule to induce aggregation and self-assembly of the metal charged complex through metal . . . metal interactions, π . . . π interactions, or a combination of both type of interactions wherein the metal complex comprises at least one transition metal, at least one carbon donor ligand, and one nitrogen donor ligand, and wherein the carbon donor ligand has the following structure:

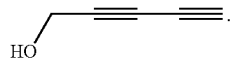

2. The composition of claim 1, wherein the self-assembly creates one or more optical property changes to the metal complex.

3. The composition of claim 2, wherein the one or more optical property changes are UV/vis, emission, or CD intensity changes.

4. The composition of claim 1, wherein the multiple-charged biomolecule carries no less than three net charges.

5. The composition of claim 1, wherein the multiple-charged biomolecule is a single-stranded nucleic acid.

6. The composition of claim 1, wherein the at least one transition metal is platinum (Pt), gold (Au), palladium (Pd), rhodium (Rh), iridium (Ir), or silver (Ag).

7. The composition of claim 1, wherein the nitrogen donor ligand is pyridine, bipyridine, terpyridine, polypyridine, arylpyridine, diarylpyridine, arylbipyridine, phenanthroline, diazine, triazine, phthalocyanine, imine, diimine, triimine, or porphyrin.

8. The composition of claim 1, wherein the metal complex has a planar structure or a partially planar structure capable of π . . . π stacking interactions.

9. An assay method for detecting the presence of a target multiple-charged biomolecule in a sample comprising:
   (a) combining a charged $d^8$ or $d^{10}$ metal complex as set forth in claim 1, wherein the metal complex comprising at least one transition metal and at least one corresponding coordinating ligand, with the sample potentially containing the target multiple-charged biomolecule under conditions effective to allow the $d^8$ or $d^{10}$ metal complex and the target multiple-charged biomolecule to bind to each other by electrostatic interactions, and to allow subsequent self-assembly of a charged $d^8$ or $d^{10}$ metal complex aggregate, and
   (b) measuring optical properties of the charged $d^8$ or $d^{10}$ metal complex aggregate.

10. A kit for use in detecting a multiple-charged biomolecule in a sample comprising:
   (a) a composition comprising a charged $d^8$ or $d^{10}$ metal complex as set forth in claim 1, wherein the metal complex electrostatically binds to the multiple-charged biomolecule to induce aggregation and self-assembly of the $d^8$ or $d^{10}$ metal complex through metal . . . metal interactions and π . . . π interactions, and
   (b) instructions for use.

* * * * *